US008278106B2

(12) United States Patent
Martinson et al.

(10) Patent No.: US 8,278,106 B2
(45) Date of Patent: Oct. 2, 2012

(54) ENCAPSULATION OF PANCREATIC CELLS DERIVED FROM HUMAN PLURIPOTENT STEM CELLS

(75) Inventors: Laura Martinson, San Diego, CA (US); Chad Green, San Diego, CA (US); Evert Kroon, San Diego, CA (US); Alan Agulnick, San Diego, CA (US); Olivia Kelly, San Diego, CA (US); Emmanuel E. Baetge, Encinitas, CA (US)

(73) Assignee: Viacyte, Inc., San Diego, CA (US)

( * ) Notice: Subject to any disclaimer, the term of this patent is extended or adjusted under 35 U.S.C. 154(b) by 0 days.

(21) Appl. No.: 12/618,659

(22) Filed: Nov. 13, 2009

(65) Prior Publication Data

US 2010/0124564 A1    May 20, 2010

Related U.S. Application Data

(60) Provisional application No. 61/114,857, filed on Nov. 14, 2008, provisional application No. 61/121,086, filed on Dec. 9, 2008.

(51) Int. Cl.
*C12N 5/00* (2006.01)
*C12N 5/08* (2006.01)
*C12M 1/00* (2006.01)
*C12M 1/12* (2006.01)

(52) U.S. Cl. ............. 435/377; 435/289.1; 435/297.1; 435/371

(58) Field of Classification Search ............ 435/371, 435/377, 289.1, 297.1
See application file for complete search history.

(56) References Cited

U.S. PATENT DOCUMENTS

| | | | |
|---|---|---|---|
| 4,542,104 A | 9/1985 | Stryer et al. | |
| 5,011,494 A | 4/1991 | von Recum et al. | |
| 5,100,392 A | 3/1992 | Orth et al. | |
| 5,171,846 A | 12/1992 | Gupta | |
| 5,219,361 A | 6/1993 | von Recum et al. | |
| 5,240,640 A | 8/1993 | Siiman et al. | |
| 5,248,772 A | 9/1993 | Siiman et al. | |
| 5,272,257 A | 12/1993 | Gupta | |
| 5,314,471 A | 5/1994 | Brauker et al. | |
| 5,324,518 A | 6/1994 | Orth et al. | |
| 5,344,454 A | 9/1994 | Clarke et al. | |
| 5,421,923 A | 6/1995 | Clarke et al. | |
| 5,453,278 A | 9/1995 | Chan et al. | |
| 5,453,357 A | 9/1995 | Hogan | |
| 5,466,609 A | 11/1995 | Siiman et al. | |
| 5,527,713 A | 6/1996 | Bolton et al. | |
| 5,529,914 A | 6/1996 | Hubbell et al. | |
| 5,545,223 A | 8/1996 | Neuenfeldt et al. | |
| 5,549,675 A | 8/1996 | Neuenfeldt et al. | |
| 5,552,086 A | 9/1996 | Siiman et al. | |
| 5,569,462 A | 10/1996 | Martinson et al. | |
| 5,593,440 A | 1/1997 | Brauker et al. | |
| 5,639,620 A | 6/1997 | Siiman et al. | |
| 5,653,756 A | 8/1997 | Clarke et al. | |
| 5,658,741 A | 8/1997 | Bolton et al. | |
| 5,670,372 A | 9/1997 | Hogan | |
| 5,690,926 A | 11/1997 | Hogan | |
| 5,707,877 A | 1/1998 | Siiman et al. | |
| 5,713,888 A | 2/1998 | Neuenfeldt et al. | |
| 5,733,336 A | 3/1998 | Neuenfeldt et al. | |
| 5,741,330 A | 4/1998 | Brauker et al. | |
| 5,776,706 A | 7/1998 | Siiman et al. | |
| 5,782,912 A | 7/1998 | Brauker et al. | |
| 5,800,529 A | 9/1998 | Brauker et al. | |
| 5,801,033 A | 9/1998 | Hubbell et al. | |
| 5,807,406 A | 9/1998 | Brauker et al. | |
| 5,882,354 A | 3/1999 | Brauker et al. | |
| 5,902,745 A | 5/1999 | Butler et al. | |
| 5,945,293 A | 8/1999 | Siiman et al. | |
| 5,964,261 A * | 10/1999 | Neuenfeldt et al. | 141/327 |
| 5,964,804 A | 10/1999 | Brauker et al. | |
| 5,989,833 A | 11/1999 | Charon et al. | |
| 6,060,640 A | 5/2000 | Pauley et al. | |
| 6,074,884 A | 6/2000 | Siiman et al. | |
| 6,156,305 A | 12/2000 | Brauker et al. | |
| 6,200,806 B1 | 3/2001 | Thomson | |
| 6,251,671 B1 | 6/2001 | Hogan et al. | |
| 6,258,870 B1 | 7/2001 | Hubbell et al. | |
| 6,365,385 B1 | 4/2002 | Opara | |
| 6,520,997 B1 | 2/2003 | Pekkarinen et al. | |
| 6,773,458 B1 | 8/2004 | Brauker et al. | |
| 6,800,480 B1 | 10/2004 | Bodnar et al. | |

(Continued)

FOREIGN PATENT DOCUMENTS

EP    0 438 520    7/1991

(Continued)

OTHER PUBLICATIONS

Amano et al., "Representation of tooth pulp in the mesencephalic trigeminal nucleus and the trigeminal ganglion in the cat, as revealed by retrogradely transported horseradish peroxidase," *Neruosci. Letter*, (1987) 82(2):127-32.

(Continued)

*Primary Examiner* — Shin-Lin Chen
(74) *Attorney, Agent, or Firm* — Knobbe, Martens, Olson & Bear, LLP

(57) ABSTRACT

The present invention relates to methods for encapsulating pancreatic progenitors in a biocompatible semi-permeable encapsulating device. The present invention also relates to production of human insulin in a mammal in response to glucose stimulation.

16 Claims, 11 Drawing Sheets

U.S. PATENT DOCUMENTS

| | | | |
|---|---|---|---|
| 6,911,227 | B2 | 6/2005 | Hubbell et al. |
| 7,217,569 | B2 | 5/2007 | Thomson |
| 7,413,902 | B2 | 8/2008 | Bodnar |
| 7,427,415 | B2 | 9/2008 | Scharp et al. |
| 7,432,104 | B2 | 10/2008 | Mitalipova et al. |
| 7,510,876 | B2 | 3/2009 | D'Amor et al. |
| 7,534,608 | B2 * | 5/2009 | Martinson et al. ............ 435/377 |
| 7,541,185 | B2 | 6/2009 | D'Amour et al. |
| 7,625,753 | B2 | 12/2009 | Kelly et al. |
| 7,695,965 | B2 * | 4/2010 | Martinson et al. ............ 435/377 |
| 2002/0049426 | A1 | 4/2002 | Butler et al. |
| 2005/0266554 | A1 | 12/2005 | D'Amour et al. |
| 2006/0003446 | A1 | 1/2006 | Keller et al. |
| 2006/0063141 | A1 | 3/2006 | McGann et al. |
| 2006/0182722 | A1 | 8/2006 | Hering et al. |
| 2007/0026515 | A1 | 2/2007 | Newman et al. |
| 2007/0122905 | A1 | 5/2007 | D'Amour et al. |
| 2007/0154984 | A1 | 7/2007 | D'Amour et al. |
| 2007/0254359 | A1 | 11/2007 | Rezania et al. |
| 2007/0259421 | A1 | 11/2007 | D'Amour et al. |
| 2008/0268534 | A1 | 10/2008 | Robins et al. |
| 2009/0004152 | A1 | 1/2009 | Martinson et al. |
| 2009/0093372 | A1 | 4/2009 | Agulnick et al. |
| 2009/0104696 | A1 | 4/2009 | Robins et al. |
| 2009/0263896 | A1 | 10/2009 | Kelly et al. |
| 2010/0112691 | A1 | 5/2010 | Green et al. |

FOREIGN PATENT DOCUMENTS

| | | |
|---|---|---|
| WO | WO 90/07380 | 7/1990 |
| WO | WO 96/26782 | 9/1996 |
| WO | WO 99/53021 | 10/1999 |
| WO | WO 03/059072 | 7/2003 |
| WO | WO 2005/021728 | 3/2005 |
| WO | WO 2007/101130 | 9/2007 |

OTHER PUBLICATIONS

Borowiak et al., "Small molecules efficiently direct endodermal differentiation of mouse and human embryonic stem cells," *Cell Stem Cell*, (2009) 4(4):348-58.

Bunn et al., "Small cell lung cancer, endocrine cells of the fetal bronchus, and other neuroendocrine cells express the Leu-7 antigenic determinant present on natural killer cells," *Blood*, (1985) 65:764-768.

Collier et al., "Intracerebral grafting and culture of cryopreserved primate dopamine neurons," *Brain Res.*, (1987) 436(2):363-6.

Cowan et al., "Derivation of embryonic stem-cell lines from human blastocysts," *N. Engl. J. Med.*, (2004) 350(13):1353-6.

D'Amour et al. "Production of Pancreatic Hormone-Expressing Endocrine Cells From Human Embryonic Stem Cells" (Nov. 1, 2006) Nature Biotechnology 24, 1392-1401.

D'Amour et al., "Efficient differentiation of human embryonic stem cells to definitive endoderm." Nature Biotechnology, Dec. 2005, vol. 23, No. 12, pp. 1534-1541.

Edwards et al., "Plug flow cytometry: An automated coupling device for rapid sequential flow cytometric sample analysis," *Cytometry*, (1999) 37(2):156-9.

Gage et al., "Rat fetal brain tissue grafts survive and innervate host brain following five day pregraft tissue storage," *Neurosci. Lett.*, (1985), 60(2):133-7.

Hasegawa et al., "A method for the selection of human embryonic stem cell sublines with high replating efficiency after single-cell dissociation," *Stem Cells*, (2006) 24(12):2649-60.

Johansson et al, "Tissue factor produced by the endocrine cells of the islets of langerhans is associated with a negative outcome of clinical islet transportation," *Diabetes*, (2005) 54:1755-1762.

Köhler et al., "Continuous cultures of fused cells secreting antibody of predefined specificity," *Nature*, (1975) 256(5517) 495-7.

Kroon et al., "Pancreatic endoderm derived from human embryonic stem cells generates glucose-responsive insulin-secreting cells in vivo," *Nat. Biotechnol.*, (2008), 26(4):443-52.

McLean et al. "Activin A Efficiently Specifies Definitive Endoderm from Human Embryonic Stem Cells Only When Phosphtidylinositol 3-Kinase Signaling Is Suppressed" (2007) Stem Cells 25: 29-38.

Sauer et al., "Effects of Cool Storage on Survival and Function of Intrastriatal Ventral Mesencephalic Grafts," *Restorative Neurology and Neuroscience*, (1991), 2:123-135.

Siiman et al., "Immunophenotyping using gold or silver nanoparticle-polystyrene bead conjugates with multiple light scatter," *Cytometry*, (2000) 41(4):298-307.

Siiman et al., "Preparation, Microscopy, and Flow Cytometry with Excitation into Surface Plasmon Resonance Bands of Gold or Silver Nanoparticles on Aminodextran-Coated Polystyrene Beads," *J. Phys. Chem.*, (2000) 104:9795-9810.

Stark et al., "FGFR-4, a new member of the fibroblast growth factor receptor family, expressed in the definitive endoderm and skeletal muscle lineages of the mouse," *Development*, (1991) 113:641-651.

Suscheck et al., "Primary cultures of rat islet capillary endothelial cells," *Am. J. Pathol.*, (1994) 145(3):685-695.

Takahashi et al., "Induction of pluripotent stem cells from adult human fibroblasts by defined factors," *Cell*, (2007) 131(5):861-72.

Takahashi et al., "Induction of pluripotent stem cells from mouse embryonic and adult fibroblast cultures by defined factors," *Cell*, (2006) 126(4):663-76.

Yu et al., "Human induced pluripotent stem cells free of vector and transgene sequences," *Science*, (2009) 324(5928):797-801.

Yu et al., "Induced pluripotent stem cell lines derived from human somatic cells," *Science*, (2009) 318(5858):1917-20.

Zhou et al., "Generation of induced pluripotent stem cells using recombinant proteins," *Cell Stem Cell*, (2009) 4(5):381-4.

International Search Report and Written Opinion issued in International Application No. PCT/US2007/080589, dated Jun. 17, 2008.

International Search Report and Written Opinion issued in International Application No. PCT/US2009/064459, dated Oct. 4, 2010.

* cited by examiner

ENCAPSULATION OF PANCREATIC CELLS DERIVED FROM HUMAN PLURIPOTENT STEM CELLS

CROSS REFERENCE TO RELATED APPLICATIONS

This application is a nonprovisional application which claims priority under 35 U.S.C.§119(e) to U.S. Provisional Patent Application No. 61/114,857, entitled ENCAPSULATION OF PANCREATIC PROGENITORS DERIVED FROM HES CELLS, filed Nov. 14, 2008; and U.S. Provisional Patent Application No. 61/121,086, entitled ENCAPSULATION OF PANCREATIC ENDODERM CELLS, filed Dec. 9, 2008. The disclosure of each of the above-listed priority applications is incorporated herein by reference in its entirety.

FIELD OF THE INVENTION

The present invention relates to the fields of medicine and cell biology. In particular, the present invention relates to the encapsulation of cells derived from human embryonic stem cells and other pluripotent human cells.

BACKGROUND OF THE INVENTION

Human embryonic stem (hES) cells and induced pluripotent stem (iPS) cells from adult differentiated cells are uniquely suited for cell therapy applications because they are pluripotent and self-renewable. Owing to the large variety of cell types that can arise in differentiating pluripotent stem cell cultures, success in achieving efficient, directed differentiation is useful for therapeutic application of human pluripotent stem cells. Efficient directed differentiation of human pluripotent stem cells to various intermediate cell types including pancreatic lineage cells using various growth and signaling factors and small molecules is necessary.

SUMMARY OF THE INVENTION

Embodiments described herein relate to methods of producing insulin in a mammal by providing an implantable chamber into a host mammal, providing a pancreatic progenitor cell derived from human pluripotent stem cell (e.g., hES or iPS cells) to said chamber, maturing the pancreatic progenitor cell to a mature pancreatic hormone secreting cell, wherein the pancreatic hormone secreting cell is an insulin secreting cell which produces insulin in response to glucose stimulation in vivo, thereby producing insulin in vivo in the mammal. In some embodiments, the chamber is implanted into the mammal prior to introducing the pancreatic progenitor cell. In other embodiments, the chamber is allowed to vascularize prior to introducing the pancreatic progenitor cell. In yet other embodiments, the cell is introduced into the chamber prior to implantation.

One embodiment relates to a method for producing insulin in a mammal, comprising: (a) providing a human PDX1-positive pancreatic progenitor cell population into an implantable semi-permeable device; (b) maturing the cell population in said device to an islet, wherein the islet comprises endocrine and acinar cells, and wherein the endocrine cell is at least an insulin secreting cell which produces insulin in response to glucose stimulation in vivo, thereby producing insulin in vivo to the mammal.

Another embodiment relates to a cell encapsulating assembly for implanting a cell population into a mammalian host. In one aspect, the assembly comprises a sealed periphery defining at least one chamber for encapsulating living cells. In another aspect, the assembly comprises a wall means having a peripheral edge, wherein the assembly comprises a first seal at the peripheral edge of the wall means, thereby forming the encapsulating assembly. In some aspects, the assembly comprises a second seal which effectively reduces the chamber volume.

Another embodiment relates to a cryopreserved human pancreatic progenitor cell population. In one aspect of the embodiment, the cell population is suitable for transplantation into a mammal.

Another embodiment relates to a method of obtaining a population of cells suitable for transplantation. In one aspect of the embodiment, cells suitable for transplantation are obtained by a method comprising: a) contacting a population of human pancreatic progenitor cells with a cryopreservation solution to thereby obtain a population of cells for cryopreservation; b) decreasing the temperature of the progenitor cells for cryopreservation to about $-196°$ C. to obtain cryopreserved cells; and c) increasing the temperature of the cryopreserved cells to thereby obtain a population of pancreatic progenitor cells suitable for transplantation. In some embodiments the temperature of the progenitor cells for cryopreservation is decreased to less than $0°$ C., $-10°$ C., $-20°$ C., $-30°$ C., $-40°$ C., $-50°$ C., $-60°$ C., $-70°$ C., $-80°$ C., $-90°$ C., $-100°$ C., $-110°$ C., $-120°$ C., $-130°$ C., $-140°$ C., $-150°$ C., $-160°$ C., $-170°$ C., $-180°$ C., $-190°$ C., $-200°$ C., $-210°$ C., $-220°$ C., $-230°$ C., $-240°$ C., $-250°$ C., or $-260°$ C.

DETAILED DESCRIPTION OF THE PREFERRED EMBODIMENT

Figure 1:
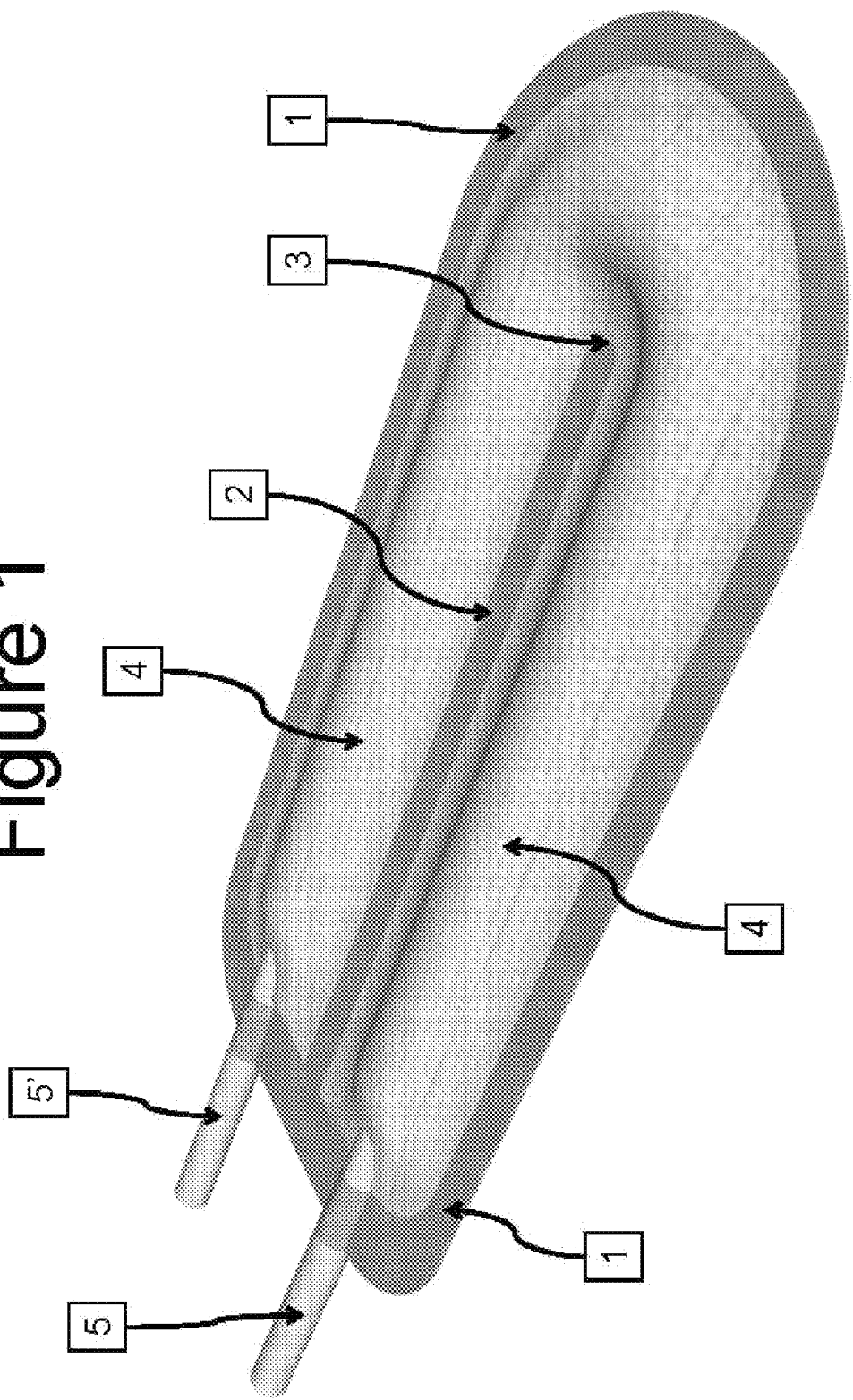
FIG. 1 is a perspective view of a dual ported encapsulation device with an internal ultrasonic weld to compartmentalize the main lumen.
Figure 2:
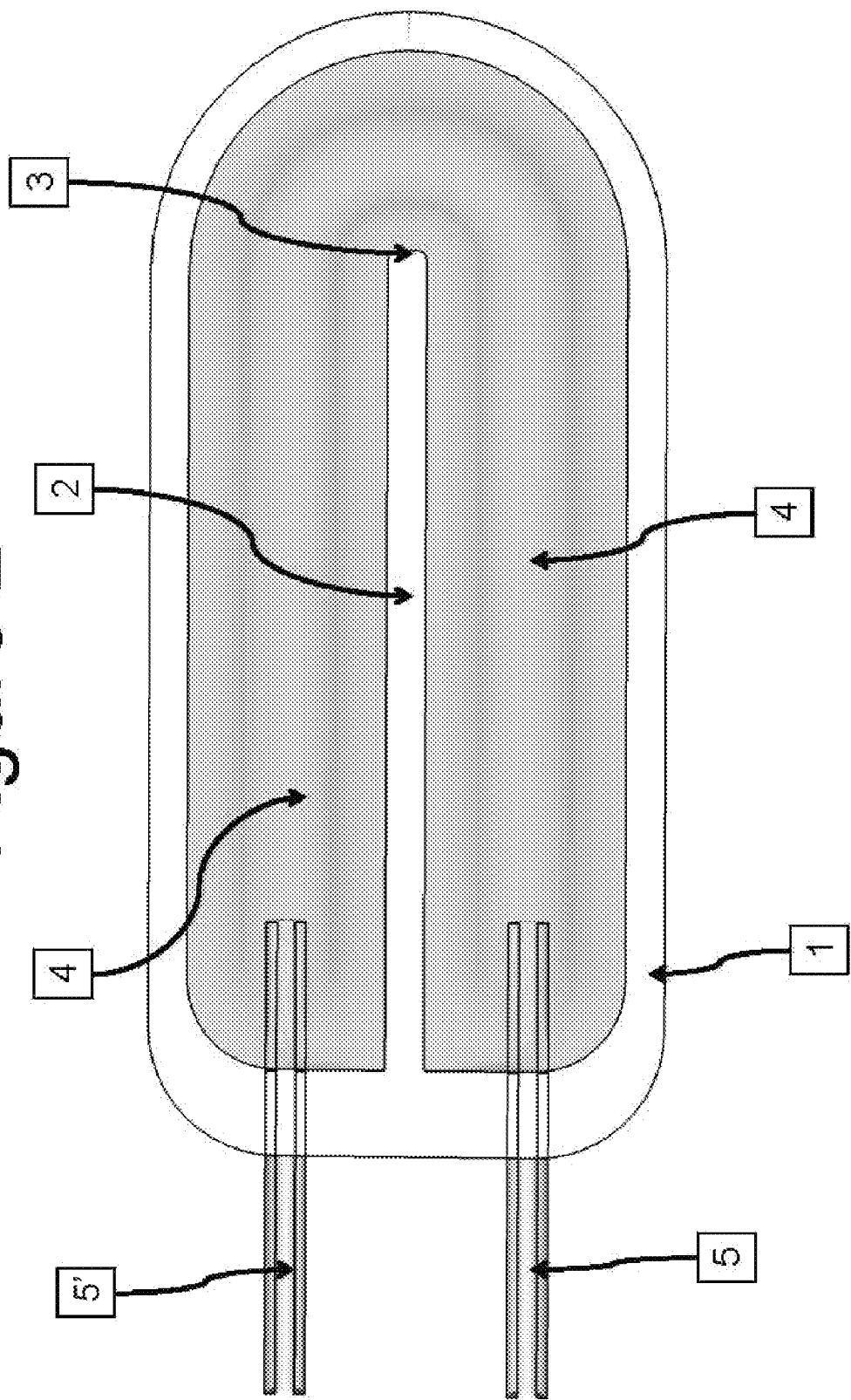
FIG. 2 is a top section view of the encapsulation device shown in FIG. 1
Figure 3:
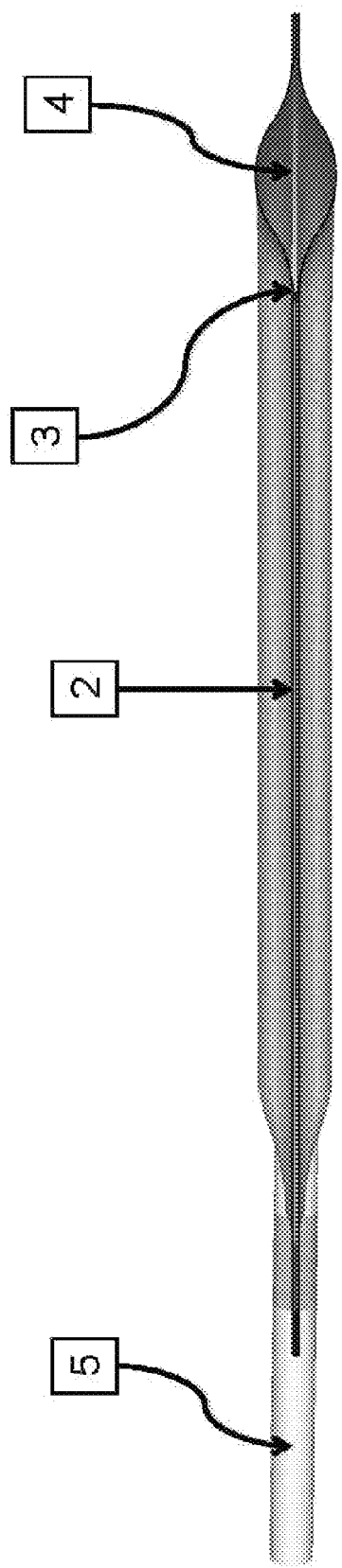
FIG. 3 is a side view of the encapsulation device shown in FIG. 1 with a cross section taken through the center of the device along the internal ultrasonic weld region.
Figure 4:
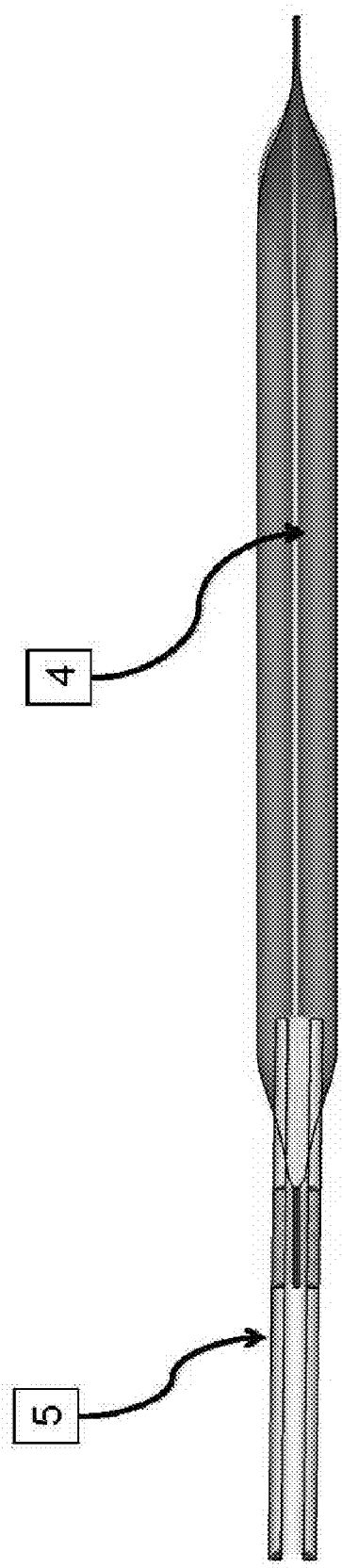
FIG. 4 is a side view of the encapsulation device shown in FIG. 1 with a cross section taken through the center of a compartmentalized lumen along the axis of the port.
Figure 5:
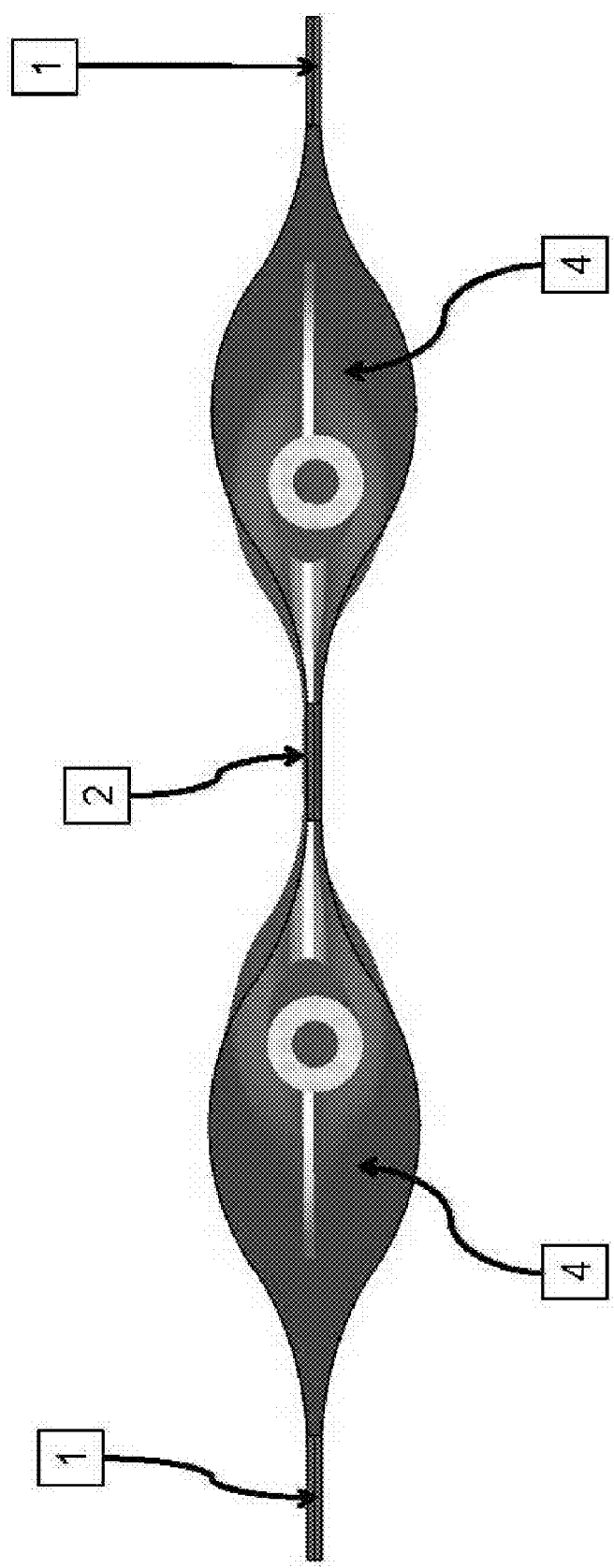
FIG. 5 is an end view of the encapsulation device shown in FIG. 1 with a cross section taken through the compartmentalized lumens.

Embodiments described herein are directed to methods of producing insulin in vivo by implanting in a mammal human pancreatic progenitor cells derived from human embryonic stem cells in encapsulating devices, including a bio-compatible polyethylene glycol-based device and a mechanical/medical device.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

In one embodiment, hES-derived cells are encapsulated using a bio-compatible polyethylene glycol (PEG). PEG-based encapsulation is described in more detail in U.S. Pat. No. 7,427,415, entitled IMPLANTATION OF ENCAPSULATED BIOLOGICAL MATERIALS FOR TREATING DISEASES; U.S. Pat. No. 6,911,227, entitled GELS FOR ENCAPSULATION OF BIOLOGICAL MATERIALS; and U.S. Pat. Nos. 6,911,227, 5,529,914, 5,801,033, 6,258,870, entitled GELS FOR ENCAPSULATION OF BIOLOGICAL MATERIALS, which is herein incorporated by reference in their entireties.

In another embodiment, the encapsulating device is a TheraCyte device (Irvine, Calif.). TheraCyte cell encapsulation devices are further described in U.S. Pat. Nos. 6,773,458; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518; 5,219,361; 5,100,392; and 5,011,494, which are all herein incorporated in their entireties by reference in their entireties.

In one embodiment, methods are described for producing hES cell aggregate suspensions from a single cell suspension of pluripotent stem cell cultures or hES-derived cell cultures. The pluripotent stem cell can be initially cultured on fibroblast feeders, or they can be feeder-free. Methods of isolating hESC and culturing such on human feeder cells was described in U.S. Pat. No. 7,432,104 entitled METHODS FOR THE CULTURE OF HUMAN EMBRYONIC STEM CELLS ON HUMAN FEEDER CELLS, which is herein incorporated by reference in its entirety. Various methods for producing hES cell aggregate suspension cultures and/or hES-derived cell aggregate suspension cultures are described in detail in U.S. application Ser. No. 12/264,760, entitled STEM CELL AGGREGATE SUSPENSION COMPOSITIONS AND METHODS OF DIFFERENTIATION THEREOF, filed Oct. 4, 2008, which is herein incorporated by reference in its entirety.

The differentiation culture conditions and hES-derived cell types described herein are substantially similar to that described in D'Amour et al. 2006, supra or those described in U.S. Pat. No. 7,534,608; U.S. patent application Ser. No. 11/681,687, filed Mar. 2, 2007; and Ser. No. 11/773,944, filed Jul. 5, 2007, the disclosures of which are incorporated herein by reference in their entireties. D'Amour et al. describe a 5 step differentiation protocol: stage 1 (results in mostly definitive endoderm production), stage 2 (results in mostly PDX1-negative foregut endoderm production), stage 3 (results in mostly PDX1-positive foregut endoderm production), stage 4 (results in mostly pancreatic endoderm or pancreatic endocrine progenitor production) and stage 5 (results in mostly hormone expressing endocrine cell production).

As used herein, "definitive endoderm (DE)" refers to a multipotent endoderm lineage cell that can differentiate into cells of the gut tube or organs derived from the gut tube. In accordance with certain embodiments, the definitive endoderm cells are mammalian cells, and in a preferred embodiment, the definitive endoderm cells are human cells. In some embodiments, definitive endoderm cells express or fail to significantly express certain markers. In some embodiments, one or more markers selected from CER, FOZA2, SOX17, CXCR4, M1XL1, GATA4, HNF3-β, GSC, FGF17, VWF, CALCR, FOXQ1, CMKOR1 and CRIP1 are expressed in definitive endoderm cells. In other embodiments, one or more markers selected from OCT4, α-fetoprotein (AFP), Thrombomodulin (TM), SPARC, SOX7 and HNF4-α are not significantly expressed in definitive endoderm cells. To be clear, a definitive endoderm cell is distinguished from other endoderm-lineage cells, such as foregut endoderm or gut endoderm or PDX1-negative foregut endoderm cells, which appreciably express HNF4-α as compared to definitive endoderm. Definitive endoderm cell populations and methods of production thereof are also described in U.S. Pat. No. 7,510,876, entitled DEFINITIVE ENDODERM, which is hereby incorporated in its entirety.

Still other embodiments relate to cell cultures termed "PDX1-negative foregut endoderm cells" or "foregut endoderm cells" or "gut endoderm" or equivalents thereof. In some embodiments, the foregut endoderm cells express SOX17, HNF1-13, HNF4-α and FOXA1 markers but do not substantially express PDX1, AFP, SOX7, SOX1. PDX1-negative foregut endoderm cell populations and methods of production thereof are also described in U.S. application Ser. No. 11/588,693, entitled PDX1-expressing dorsal and ventral foregut endoderm, filed Oct. 27, 2006 which is incorporated herein by reference in its entirety. Again, gut endoderm appreciably expresses HNF4-α as compared to the definitive endoderm cells, or Stage 1 cells; see Examples below.

Other embodiments described herein relate to cell cultures of "PDX1-positive, dorsally-biased, foregut endoderm cells", "PDX1-positive foregut endoderm cells", or "PDX1-positive endoderm" or equivalents thereof. In some embodiments, the PDX1-positive foregut endoderm cells express PDX1, HNF6, SOX 9 and PROX1 markers but do not substantially express NKX6.1, PTF1A, CPA, cMYC, SOX17, HNF1B or HNF4alpha. PDX1-positive foregut endoderm cell populations and methods of production thereof are also described in U.S. application Ser. No. 11/588,693, entitled PDX1-expressing dorsal and ventral foregut endoderm, filed Oct. 27, 2006, which is incorporated herein by reference in its entirety.

Other embodiments described herein relate to cell cultures of "pancreatic progenitors", "PDX1-positive pancreatic endoderm cells," "PDX1-positive pancreatic progenitor," "pancreatic epithelium", "PE" or equivalents thereof. PDX1-positive pancreatic progenitor cells are multipotent and can give rise to various cells in the pancreas including but not limited to acinar, duct and endocrine cells. In some embodiments, the PDX1-positive pancreatic progenitor cells express increased levels of PDX1 and NKX6.1 as compared to non pre-pancreatic endoderm cells which do not appreciably express these markers. PDX1-positive pancreatic progenitor cells also express low to no levels of PTF1A, CPA, cMYC, NGN3, PAX4, ARX and NKX2.2, INS, GCG, GHRL, SST, and PP.

Alternatively, other embodiments relate to cell cultures of "PDX1-positive pancreatic endoderm tip cells," or equivalents thereof. In some embodiments, the PDX1-positive pancreatic endoderm tip cells express increased levels of PDX1 and NKX6.1 similar to PDX1-positive pancreatic progenitor cells, but unlike PDX1-positive pancreatic progenitor cells, PDX1-positive pancreatic endoderm tip cells additionally express increased levels of PTF1A, CPA and cMYC. PDX1-positive pancreatic endoderm tip cells also express low to no levels of NGN3, PAX4, ARX and NKX2.2, INS, GCG, GHRL, SST, and PP.

Other embodiments relate to cell cultures of "pancreatic endocrine precursor cells," "pancreatic endocrine progenitor cells" or equivalents thereof. Pancreatic endocrine progenitor cells are multipotent and give rise to mature endocrine cells including alpha, beta, delta and PP cells. In some embodiments, the pancreatic endocrine progenitor cells express increased levels of NGN3, PAX4, ARX and NKX2.2 as compared to other non-endocrine progenitor cell types. Pancreatic progenitor cells also express low to no levels of INS, GCG, GHRL, SST, and PP.

Still other embodiments relate to cell cultures of "pancreatic endocrine cells," "pancreatic hormone secreting cells", "pancreatic islet hormone-expressing cell," or equivalents thereof refer to a cell, which has been derived from a pluripotent cell in vitro, e.g. alpha, beta, delta and/or PP cells or combinations thereof. The endocrine cells can be poly-hormonal or singly-hormonal, e.g. expressing insulin, glucagon, ghrelin, somatostatin and pancreatic polypeptide or combinations thereof. The endocrine cells can therefore express one or more pancreatic hormones, which have at least some of the functions of a human pancreatic islet cell. Pancreatic islet hormone-expressing cells can be mature or immature. Immature pancreatic islet hormone-expressing cells can be distinguished from mature pancreatic islet hormone-expressing cells based on the differential expression of certain markers, or based on their functional capabilities, e.g., glucose responsiveness in vitro or in vivo. Pancreatic endocrine cells also express low to no levels of NGN3, PAX 4, ARX and NKX2.2.

Most of above cell types are epithelialized as compared to mesenchymal definitive endoderm cells. In some embodiments, the pancreatic endoderm cells express one or more markers selected from Table 3 and/or one or more markers selected from Table 4 of related U.S. application Ser. No. 11/588,693 entitled PDX1 EXPRESSING DOSAL AND VENTRAL FOREGUT ENDODERM, filed Oct. 27, 2006, and also U.S. application Ser. No. 11/115,868, entitled PDX1-expressing endoderm, filed Apr. 26, 2005, which are hereby incorporated herein by reference in their entireties.

In certain embodiments, the terms "enriched", "isolated", "separated", "sorted", "purified" or purifying by depleting or equivalents thereof refer to a cell culture or a cell population or cell sample that contains at least 15%, 20%, 25%, 30%, 35%, 40%, 45%, 50%, 55%, 60%, 65%, 70%, 75%, 80%, 85%, 90%, 95%, 96%, 97%, 98%, 99% or 100% of the desired cell lineage or a desired cell having a certain cell phenotype, e.g., expressing a certain cell marker or not expressing a certain cell marker gene characteristic of that cell phenotype. Methods for purifying, enriching, isolating, separating, sorting, and/or depleting endoderm lineage cells derived from hES cells are also described in U.S. application Ser. No. 12/107,020, entitled METHODS FOR PURIFYING ENDODERM AND PANCREATIC ENDODERM CELLS DERIVED FROM HUMAN EMBRYONIC STEM CELLS, filed Apr. 21, 2008 which is incorporated herein by reference in its entirety.

As used herein, the term "contacting" (i.e., contacting a cell e.g., a differentiable cell, with a compound) is intended to include incubating the compound and the cell together in vitro (e.g., adding the compound to cells in culture). The term "contacting" is not intended to include the in vivo exposure of cells to a defined cell medium comprising an ErbB3 ligand, and optionally, a member of the TGF-β family, that may occur naturally in a subject (i.e., exposure that may occur as a result of a natural physiological process). The step of contacting the cell with a defined cell medium comprising an ErbB3 ligand, and optionally, a member of the TGF-β family, can be conducted in any suitable manner. For example, the cells may be treated in adherent culture, or in suspension culture. It is understood that the cells contacted with the defined medium can be further treated with a cell differentiation environment to stabilize the cells, or to differentiate the cells.

As used herein, the term "differentiate" refers to the production of a cell type that is more differentiated than the cell type from which it is derived. In some embodiments, the term "differentiate" means to produce a cell that has fewer fate choices than the cell from which it was derived. The term therefore encompasses cell types that are partially and terminally differentiated. Differentiated cells derived from hES cells are generally referred to as hES-derived cells or hES-derived cell aggregate cultures, or hES-derived single cell suspensions, or hES-derived cell adherent cultures and the like.

As used herein, the term "differentiable cell" is used to describe a cell or population of cells that can differentiate into at least partially mature cells, or that can participate in the differentiation of cells, e.g., fuse with other cells, that can differentiate into at least partially mature cells. As used herein, "partially mature cells", "progenitor cells", "immature cells", "precursor cells", "multipotent cells" or equivalents thereof include those cells which are not terminally differentiated, e.g., definitive endoderm cells, PDX1-negative foregut endoderm cells, PDX1-positive pancreatic endoderm cells which further include PDX1-positive pre-pancreatic endoderm cells and PDX1-positive pancreatic endoderm tip cells. All are cells that exhibit at least one characteristic of the phenotype, such as morphology or protein expression, of a mature cell from the same organ or tissue but can further differentiate into at least one other cell type. For example, a normal, mature hepatocyte typically expresses such proteins as albumin, fibrinogen, α-1-antitrypsin, prothrombin clotting factors, transferrin, and detoxification enzymes such as the cytochrome P-450s, among others. Thus, as used herein, a "partially mature hepatocyte" may express albumin or another one or more proteins, or begin to take the appearance or function of a normal, mature hepatocyte.

As used herein, the term "substantially" refers to a great extent or degree, e.g. "substantially similar" in context would be used to describe one method which is to great extent or degree similar to another method. However, as used herein, the term "substantially free", e.g., "substantially free" or "substantially free from contaminants," or "substantially free of serum" or "substantially free of insulin or insulin like growth factor" or equivalents thereof, is meant that the solution, media, supplement, excipient and the like, is at least 98%, or at least 98.5%, or at least 99%, or at least 99.5%, or at least 100% free of serum, contaminants or equivalent thereof. In one embodiment, a defined culture media contains no serum, or is 100% serum-free, or is substantially free of serum. Conversely, as used herein, the term "substantially similar" or equivalents thereof is meant that the composition, process, method, solution, media, supplement, excipient and the like is meant that the process, method, solution etc., is at least 50%, 55%, 60%, 65%, 70%, 75%, 80%, at least 85%, at least 90%, at least 95%, or at least 99% similar to that previously described in the specification herein, or in a previously described process or method incorporated herein in its entirety.

Also, as used herein, in connection with the composition of a cell population, the term "essentially" or "substantially" means predominantly or mainly. In some embodiments these terms mean at least 85% of the cells in a cell population, at least 86% of the cells in a cell population, at least 87% of the cells in a cell population, at least 88% of the cells in a cell population, at least 89% of the cells in a cell population, at least 90% of the cells in a cell population, at least 91% of the cells in a cell population, at least 92% of the cells in a cell population, at least 93% of the cells in a cell population, at least 94% of the cells in a cell population, at least 95% of the cells in a cell population, at least 96% of the cells in a cell population, at least 97% of the cells in a cell population, at least 98% of the cells in a cell population, or at least 99% of the cells in a cell population. In other embodiments, the terms or phrases "essentially free of" and "substantially free of" refer to a de minimus or a reduced amount of a component or cell present in any cell culture, e.g., pancreatic progenitors as described herein are "essentially or substantially homogenous", "essentially or substantially homo-cellular", "essentially hES cells", "essentially or substantially definitive endoderm cells", "essentially or substantially foregut endoderm cells", "essentially or substantially gut endoderm cells", "essentially or substantially PDX1-negative foregut endoderm cells", "essentially or substantially PDX1-positive pre-pancreatic endoderm cells", "essentially or substantially PDX1-positive pancreatic progenitor cells", "essentially or substantially pancreatic epithelial cells", "essentially or substantially PDX1-positive pancreatic endoderm tip cells", "essentially or substantially pancreatic endocrine precursor cells", "essentially or substantially pancreatic endocrine cells" and the like. The terms, "essentially" and "substantially" can also mean that at least 50%, 55%, 60%, 65%, 70%, 75%, 80%, at least 85%, at least 90%, at least 95%, or at least 99% that cell (definitive endoderm; PDX1-negative foregut endoderm; PDX1-positive pre-pancreatic endoderm; PDX1-positive pancreatic progenitor cells; PDX1-positive pancreatic tip cells; endocrine precursor cells, and endocrine hormone-secreting cells).

As used herein, the term "effective amount" or equivalents thereof of a compound refers to that concentration of the compound that is sufficient in the presence of the remaining components of the defined medium to effect the stabilization of the differentiable cell in culture for greater than one month in the absence of a feeder cell and in the absence of serum or serum replacement. This concentration is readily determined by one of ordinary skill in the art.

As used herein, the term "express" refers to the transcription of a polynucleotide or translation of a polypeptide in a cell, such that levels of the molecule are measurably higher in a cell that expresses the molecule than they are in a cell that does not express the molecule. Methods to measure the expression of a molecule are well known to those of ordinary skill in the art, and include without limitation, Northern blotting, RT-PCR, in situ hybridization, Western blotting, and immunostaining.

As used herein when referring to a cell, cell line, cell culture or population of cells, the term "isolated" refers to being substantially separated from the natural source of the cells such that the cell, cell line, cell culture, or population of cells are capable of being cultured in vitro. In addition, the term "isolating" is used to refer to the physical selection of one or more cells out of a group of two or more cells, wherein the cells are selected based on cell morphology and/or the expression of various markers.

As used herein, the term "preserving cells" means maintaining cells in a viable state for a period of time before transplantation. The period of time may be 1 hour, 2 hours, 5 hours, 10 hours, 15 hours, 20 hours, 24 hours, 2 days, 4 days, 5 days, 1 week, 2 weeks, 4 weeks, 1 month, 2 months, 4 months, 6 months, 8 months, 10 months, 1 year, 2 years, 4 years, 6 years, 8 years, 10 years, 12 years, 14 years, 16 years, 18 years, 20 years, 22 years, 24 years, 30 years, 35 years, 40 years, 45 years, or 100 years or any period of time between any times provided in this range.

Differentiable cells, as used herein, may be pluripotent, multipotent, oligopotent or even unipotent. In certain embodiments, the differentiable cells are pluripotent differentiable cells. In more specific embodiments, the pluripotent differentiable cells are selected from the group consisting of embryonic stem cells, ICM/epiblast cells, primitive ectoderm cells, primordial germ cells, and teratocarcinoma cells. In some embodiments, the differentiable cells are derived from a preimplantation embryo. In one particular embodiment, the differentiable cells are mammalian embryonic stem cells. In a more particular embodiment, the differentiable cells are human embryonic stem cells.

The cell types that differentiate from differentiable cells have several uses in various fields of research and development including but not limited to drug discovery, drug development and testing, toxicology, production of cells for therapeutic purposes as well as basic science research. These cell types express molecules that are of interest in a wide range of research fields. These include the molecules known to be required for the function of the various cell types as described in standard reference texts. These molecules include, but are not limited to, cytokines, growth factors, cytokine receptors, extracellular matrix, transcription factors, secreted polypeptides and other molecules, and growth factor receptors.

It is contemplated that differentiable cells can be differentiated through contact with a cell differentiation environment. As used herein, the term "cell differentiation environment" refers to a cell culture condition wherein the differentiable cells are induced to differentiate, or are induced to become a human cell culture enriched in differentiated cells. Preferably, the differentiated cell lineage induced by the growth factor will be homogeneous in nature. The term "homogeneous," refers to a population that contains more than approximately 50%, 60%, 70%, 80%, 85%, 86%, 87%, 88%, 89%, 90%, 91%, 92%, 93%, 94%, 95%, 96%, 97%, 98%, or 99% of the desired cell lineage.

A cell differentiating medium or environment may be utilized to partially, terminally, or reversibly differentiate the differentiable cells described herein. In accordance with the embodiments described herein, the medium of the cell differentiation environment may contain a variety of components including, for example, KODMEM medium (Knockout Dulbecco's Modified Eagle's Medium), DMEM, Ham's F12 medium, FBS (fetal bovine serum), FGF2 (fibroblast growth factor 2), KSR or hLIF (human leukemia inhibitory factor). The cell differentiation environment can also contain supplements such as L-Glutamine, NEAA (non-essential amino acids), P/S (penicillin/streptomycin), N2, B27 and β-mercaptoethanol (β-ME). It is contemplated that additional factors may be added to the cell differentiation environment, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin, high dose activin, and amnionless or variants or functional fragments thereof. TGF/BMP/GDF antagonists could also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGF), insulin, the wingless related (WNT) factor family, and the hedgehog factor family or variants or functional fragments thereof. Additional factors may be added to promote mesendoderm stem/progenitor, endoderm stem/progenitor, mesoderm stem/progenitor, or definitive endoderm stem/progenitor proliferation and survival as well as survival and differentiation of derivatives of these progenitors.

The progression of the differentiable cells to the desired cell lineage, or its maintenance in an undifferentiated state can be monitored by quantitating expression of marker genes characteristic of the desired cell lineage as well as the lack of expression of marker genes characteristic of differentiable cell types. One method of quantitating gene expression of such marker genes is through the use of quantitative PCR (Q-PCR). Methods of performing Q-PCR are well known in the art. Other methods that are known in the art can also be used to quantitate marker gene expression. Marker gene expression can be detected by using antibodies specific for the marker gene of interest.

Embodiments described herein also contemplate differentiable cells from any source within an animal, provided the cells are differentiable as defined herein. For example, differentiable cells may be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In specific embodiments, the differentiable cells are embryonic stem cells. In other specific embodiments, the differentiable cells are adult stem cells. In still other specific embodiments, the stem cells are placental- or chorionic-derived stem cells.

Other embodiments contemplate using differentiable cells from any animal capable of generating differentiable cells. The animals from which the differentiable cells are harvested may be vertebrate or invertebrate, mammalian or non-mammalian, human or non-human. Examples of animal sources include, but are not limited to, primates, rodents, canines, felines, equines, bovines and porcines.

Some embodiments contemplate using induced pluripotent stem (iPS) cells, which are pluripotent stem cells derived from a non-pluripotent cell. See Zhou et al. (2009), Cell Stem Cell 4: 381-384; Yu et al., (2009) Science 324(5928):797-801, Epub Mar. 26, 2009; Yu et al. (2007) Science 318(5858): 1917-20, Epub Nov. 20, 2007; Takahashi et al., (2007) Cell, 131:861-72; and Takahashi K. and Yamanaka S. (2006), Cell 126:663-76, which are herein incorporated by reference in their entireties. The animals from which the non-pluripotent cells are harvested may be vertebrate or invertebrate, mammalian or non-mammalian, human or non-human. Examples of animal sources include, but are not limited to, primates, rodents, canines, felines, equines, bovines and porcines.

The differentiable cells described herein can be derived using any method known to those of skill in the art. For example, human pluripotent cells can be produced using de-differentiation and nuclear transfer methods. Additionally, the human ICM/epiblast cell or the primitive ectoderm cell used herein is derived in vivo or in vitro. Primitive ectodermal cells may be generated in adherent culture or as cell aggregates in suspension culture, as described in WO 99/53021. Furthermore, the human pluripotent cells can be passaged using any method known to those of skill in the art, including, manual passaging methods, and bulk passaging methods such as enzymatic or non-enzymatic passaging.

In certain embodiment, when ES cells are utilized, the embryonic stem cells have a normal karyotype, while in other embodiments, the embryonic stem cells have an abnormal karyotype. In one embodiment, a majority of the embryonic stem cells have a normal karyotype. It is contemplated that greater than 50%, 55%, 60%, 65%, 70%, 75%, 80%, 85%, 90% or greater than 95% of metaphases examined will display a normal karyotype.

Storing Cells for Encapsulation and Transplantation

Some embodiments relate to methods for cyropreserving cells which have been cultured and/or differentiated in vitro. Such storage would allow banking, quality control, and other desired procedures and manipulations, either in connection with in vitro analysis or implantation in vivo. Methods for cell storage prior to transplantation include preserving the tissue by freezing cells (cryopreservation); or by refrigerating the cells at above freezing temperatures (hibernation). See Chanaud et al. 1987 Neurosci Lett 82: 127-133; Collier et al. (1987) 436: 363-366; and Sauer et al. 1991 Neurology and Neuroscience 2: 123-135; Gage et al. 1985 Neurosci Lett 60: 133-137, the disclosures of which are herein incorporated by reference in their entireties. Although hibernation has been reported to increase rates of graft survival and function as compared to cryopreserved tissue, cells may not be capable of long term maintenance under such conditions without jeopardizing cell viability during the hibernation period.

As used herein, a "cell suspension" or equivalents thereof refers to cell aggregates and/or clusters and/or spheres that are contacted with a medium. Such cell suspensions are described in detail in U.S. application Ser. No. 12/264,760, entitled Stem cell Aggregate Suspension Compositions and Methods of Differentiation Thereof, filed on Nov. 8, 2008, the disclosure of which is herein incorporated by reference in its entirety.

As used herein, "adapted cell suspension" or cell suspension cultures or equivalents thereof includes a cell suspension that has been stored above freezing, preferably at 4° C., in hibernation medium for about 1 hour and up to about 1, 2, 3, 4, 5, 6, 7, 8, 9, 10, 11, 12, 13, 14, 15, 16, 17, 18, 19, 20, 21, 22, 23, 24, 25 or up to 30 days.

As used herein, a cell suitable for transplantation refers to a cell or a population of cells sufficiently viable and/or functional for in vivo treatment of a metabolic disorder. For example, diabetes, or one or more symptoms thereof, can be ameliorated or reduced for a period of time following implantation of a cell suitable for transplantation into a subject suffering from diabetes. In one preferred embodiment, a cell or cell population suitable for transplantation is a pancreatic progenitor cell or population, or a PDX1-positive pancreatic progenitor cell or population, or an endocrine precursor cell or population, or a poly or singly-hormonal endocrine cell and/or any combination of cell or populations of cells, or even purified or enriched cells or populations of cells thereof. Cells suitable for the embodiments described herein are further described in detail in U.S. Pat. No. 7,534,608 the disclosure of which is herein incorporated by reference in its entirety.

As used herein the term "storing" or equivalents thereof refers to holding or maintaining cells either above or below freezing. The term is also meant to include maintaining cells prior to use in transplantation in a subject.

As used herein the term "cryopreservation" or equivalents thereof refers to preservation of cells at temperatures below freezing.

As used herein the term "hibernation" or equivalents thereof refers to preservation of cells at temperatures above freezing and sufficiently below normal physiological temperature such that one or more normal cellular physiological processes are decreased or halted. In one embodiment, preferred hibernation temperatures range between 0 and 4° C., preferably about 4° C. Hibernation medium as used herein includes any medium which lacks a cryopreservative and is physiologically compatible for storage of a cell at above freezing temperatures, preferably about 4° C.

Hibernation Conditions

Hibernation temperatures typically range from between 0 and 5° C., preferably about 4° C. Numerous types of media can be used as hibernation media in conjunction with the instant methods. Prior art methods for freezing and hibernating cells utilize complex media comprising buffers and added protein, sometimes including entirely undefined components, such as serum. However, to minimize toxicity and immunogenicity such additives are not desirable for transplantation into humans. In preferred embodiments, hibernation media is free of added $Ca^{++}$. In certain embodiments, medium for hibernating cells is free of added protein and/or free of a buffer. A preferred hibernation medium includes or consists of minimal amounts of glucose or moderate amounts of glucose in a saline solution, e.g., either no additional glucose or between about 0.1%-0.9% glucose in saline. In preferred embodiments, the hibernation medium includes or consists of about 0.1-0.5% glucose. In a more preferred embodiment, the medium includes or consists of about 0.2% glucose. In preferred embodiments, the hibernation medium includes or consists of a very small percentage (vol/vol) of NaCl, e.g., about 0.1-1% NaCl, preferably about 0.5-0.9% NaCl. In certain embodiments, more complex media can be used, e.g., Hank's balanced salt solution, Dulbecco's minimal essential medium, or Eagle's modified minimal essential medium. In certain embodiments it may be desirable to supplement the chosen hibernation medium with additives, for example, added protein (e.g., mammalian serum protein or whole serum (preferably heat inactivated)) buffers (e.g., phosphate buffers, HEPES, or the like) antioxidants, growth factors, KCl (e.g., at about 30 mM), lactate (e.g., at about 20 mM), pyruvate, $MgCl_2$ (e.g., at about 2-3 mM), sorbitol (e.g., at about 300 mM) or other additives as are well known in the art.

In certain embodiments, the cells are hibernated at about 0-5° C., preferably about 4° C. In certain embodiments, cells are maintained at about 4° C. in hibernation medium prior to freezing or use. In other embodiments, the cells are maintained at about 4° C. in hibernation medium post freezing. In still other embodiments, the cells are maintained at about 4° C. in hibernation medium without freezing. In certain embodiments, the cells are maintained in hibernation medium at about 4° C. for at least about 1 hour and up to about 1, 2, 3, 4, 5, 6, 7, 8, 9, 10, 11, 12, 13, 14, 15, 16, 17, 18, 19, 20, 21, 22, 23, 24, 25 or up to 30 days prior to freezing, post freezing or prior to use in transplantation. In other embodiments, the cells are maintained in hibernation medium at about 4° C. for at least about 12-72 hours prior to freezing, post freezing or prior to use in transplantation. In certain embodiments the cells are maintained at 4° C. in hibernation medium for at least about 24 hours prior to freezing, post freezing or prior to use in transplantation. In a more preferred embodiment, the cells are maintained in hibernation medium from at least about 36-48 hours at about 4° C. prior to freezing, post freezing or prior to use.

Cyropreservation Conditions

In some embodiments cells are cryopreserved using a cryopreservation solution. A cryopreservation solution or medium includes a solution which contains a cryopreservative, i.e., a compound which protects cells against intracellular and/or cell membrane damage as the cells are frozen or thawed. A cryopreservative is identified by enhanced viability and/or functionality of cells in contact with the cryopreservative when compared with cells which are similarly frozen or thawed in the absence of the cryopreservative. Any cryopreservative can be used in conjunction with the instant methods and the term is meant to encompass both intracellular and extracellular cryopreservatives.

Any cryopreservative known in the art can be used in a cryopreservative solution. In certain embodiments, cryopreservation solutions include intracellular cryopreservatives including but not limited to dimethylsulfoxide (DMSO), various diols and triols (e.g., ethylene glycol, propylene glycol, butanediol and triol and glycerol), as well as various amides (e.g., formamide and acetamide); and extracellular cryopreservatives including but not limited to phosphomono and phosphodiester catabolites of phosphoglycerides, polyvinylpyrrolidone, or methylcellulose (e.g., at least 0.1%) can also be used alone or in combination with any of the intracellular cryopreservatives.

In preferred embodiments, DMSO is used as the cryopreservative. DMSO can be used at a wide range of concentrations, e.g., about 1%, about 2%, about 3%, about 4%, about 5%, about 6%, about 7%, about 8%, about 9%, about 10%, about 11%, about 12%, about 13%, about 14%, about 15% or more. In more preferred embodiments the concentration of DMSO ranges from about 6% to about 12%. In particularly preferred embodiments the concentration of DMSO is about 10%.

In certain embodiments, the cryopreservative is added to the cells in a stepwise manner in order to gradually increase the concentration of the cryopreservative until the desired final concentration of cryopreservative is achieved. In certain embodiments, the cells are contacted with a cryopreservation solution containing the cryopreservative at the desired final concentration or the cryopreservative is added directly to the base medium without a gradual increase in concentration.

The cryopreservation solution includes the cryopreservative in an appropriate base medium. Any type of media can be used for this purpose. In preferred embodiments, the base medium to which the cryopreservative is added is free of added $Ca^{++}$. In certain embodiments the medium to which the cryopreservative is added is free of added protein and/or free of a buffer. In other embodiments, the base medium (e.g.

DMEM or DMEM/F12) to which the cryopreservative is added includes or consists of about 0.1-0.5% glucose or no or low glucose. In some aspects of this embodiment, the base medium (e.g. DMEM or DMEM/F12) to which the cryopreservative is added includes or consists of about 0.5-0.9% NaCl. In preferred embodiments, the base medium to which the cryopreservative is added includes or consists of very low to no glucose and about 0.5-0.9% NaCl. In another preferred embodiment, the base medium to which the cryopreservative is added includes or consists of about 0.1 to 0.2% glucose. In some aspects of this embodiment, the base medium to which the cryopreservative is added includes or consists of about 0.5-0.9% NaCl.

In certain embodiments the cryopreservation solution can also contain added protein, for example, serum, e.g., fetal calf serum or human serum, or a serum protein, e.g., albumin or knockout serum replacement. In other embodiments, the cryopreservative can also contain other additives, such as those described above for inclusion in hibernation media, for example, antioxidants, growth factors, KCl (e.g., at about 30 mM), lactate (e.g., at about 20 mM), pyruvate, $MgCl_2$ (e.g., at about 2-3 mM), sorbitol (e.g., to an osmolarity of about 300 mM) or other additives as are well known in the art.

Once the cells are suspended in cryopreservation solution, the temperature of the cells is reduced in a controlled manner. In cooling the cells to below freezing, the reduction in temperature preferably occurs slowly to allow the cells to establish an equilibrium between the intracellular and extracellular concentration of cryopreservative such that intracellular ice crystal formation is inhibited. In some embodiments, the rate of cooling is preferably fast enough to protect the cells from excess water loss and the toxic effects of cryopreservatives. The cells can then be cryopreserved at a temperature of between −20° C. and about −250° C. Preferably, the cells are stored below −90° C. to minimize the risk of ice recrystallization. In particularly preferred embodiments, the cells are cryopreserved in liquid nitrogen at about −196° C. Alternatively, controlled freezing may be accomplished with the aid of commercially available electronically controlled freezer equipment.

Thawing Conditions

After cryopreservation, the cells can be thawed through any available method. In a preferred embodiment, the cells are thawed rapidly, e.g., by quick immersion in liquid at 37° C. Once the cells are thawed, dilution of the cryopreservative is accomplished by addition of a dilution medium.

Any media can be used for diluting the cryopreservation solution which is in contact with the thawed cells. For example, any of the media listed above for use in hibernating cells, or for growth and differentiation of cells, can be used for diluting the cryopreservation solution. Other media are also appropriate, for example, Hank's balanced salt solution (preferably without Ca++), DMEM containing media with no glucose or minimal to low amounts of glucose. Additives, e.g., as listed above for inclusion in hibernation or freezing media can also be used in media for dilution. Exemplary additives include, for example, buffers (e.g., phosphate buffers, HEPES, or the like) antioxidants, growth factors, KCl (e.g., at about 30 mM), lactate (e.g., at about 20 mM), pyruvate, $MgCl_2$ (e.g., at about 2-3 mM), sorbitol (e.g., to an osmolarity of about 300 mM) or others additives as are well known in the art. Another suitable additive includes DNase (e.g., commercially available from Genentech, Incorporated as PULMOZYMEOR). The medium which is used for diluting the cryopreservation solution can, optionally, contain added protein, e.g., added protein (e.g., mammalian serum (preferably heat inactivated) or a serum protein such as albumin. In other embodiments, the medium contains no added protein and/or no added buffer.

After dilution of the cryopreservative, the cells can then be allowed to settle or a pellet of cells can be formed under centrifugal force in order to remove as much of the cryopreservation solution from the cells as possible. The cells can then be washed in medium which does not contain a cryopreservative. It may be preferable for the cells to remain at room temperature after the addition of the wash media and prior to letting the cells settle or form a pellet under centrifugal force. In preferred embodiments, the cells remain at room temperature for about 10, 15, 20, 30 minutes prior to the second centrifugation. Any medium known in the art can be used to wash the cells, for example, any of the hibernation or dilution media set forth above can be used.

After thawing and washing, cells are cultured at 37° C. for varying lengths of time to allow recovery prior to transplantation. Cells can be cultured in any culture medium, preferably in medium appropriate to their stage of differentiation. During this time some cell may death occur.

For use in transplantation, cells should be suspended in a final medium which is suitable for administration to a subject. Transplantation of cells is substantially similar to that described in U.S. Pat. No. 7,534,608, which is herein incorporated by reference in its entirety.

In addition, the thawed cells may be maintained in hibernation medium as described above at between 0 and 37° C., preferably about 4° C. for up to 1 hour and up to about 1, 2, 3, 4, 5, 6, 7, 8, 9, 10, 11, 12, 13, 14, 15, 16, 17, 18, 19, 20, 21, 22, 23, 24, 25 or up to 30 days prior to use in transplantation without a significant loss in viability. In some embodiments, no statistically significant loss in cell viability occurs.

Determining Viability of Recovered Cells

After storage, it may be desirable to assay the viability and/or functionality of the cells prior to transplantation to confirm their suitability for use, e.g., in transplantation. This can be accomplished using a variety of methods known in the art. For example, the cells can be stained using vital stains, such as, e.g., trypan blue or ethidium bromide or acridine orange. In certain embodiments, a population of cells suitable for transplantation is at least between about 50-100% viable. In preferred embodiments, a population of cells suitable for transplantation is at least about 50%, is at least about 55%, is at least about 60%, is at least about 65%, is at least about 70%, is at least about 75%, is at least about 80%, is at least about 85%, is at least about 90%, is at least about 95%, is at least about 96%, is at least about 97%, is at least about 98%, is at least about 99%, viable. In particularly preferred embodiments, such a population of cells is at least about 85% viable.

In other embodiments, the morphometric characteristics of the cells can be determined as a measure of the suitability of cells for use in transplantation. In preferred embodiments, the morphology of cells which have been stored using the instant methods and are suitable for transplantation does not differ (e.g., statistically significant) from that of fresh cells. In preferred embodiments, the in vivo morphology of cells which have been stored using the instant methods and are suitable for transplantation does not differ (e.g., statistically significant) from that of fresh cells.

In the case of cell clusters, cell mass can be quantitated before and after cell freeze/thaw and recovery. In one embodiment, cell clusters cultured in suspension can be manipulated to pack in closely. The area occupied by the clusters can then be photographed and measured. By comparing the areas occupied by cells before and after freeze/thaw and recovery, a value for percent recovery can be determined.

Cells which have been stored can also be assayed for the presence of certain hES and/or pancreatic progenitor or hormone secreting cell markers to determine if they are suitable for use in transplantation. This method has been described in detail in the above in Kroon et al. 2008, supra or in U.S. Pat. No. 7,534,608, which are herein incorporated by reference in its entireties.

Additionally, or alternatively, the cells can be tested for their functionality, e.g. as discussed in Kroon et al. 2008, supra or in U.S. Pat. No. 7,534,608, which are herein incorporated by reference in its entireties.

Encapsulation Devices

One embodiment described herein relates to encapsulation devices. Such devices can be implanted into a mammal to treat a variety of diseases and disorders. In preferred embodiments, the device comprises a biocompatible, immuno-isolating device that is capable of wholly encapsulating a therapeutically biologically active agent and/or cells therein. For example, such devices can house therapeutically effective quantities of cells within a semi-permeable membrane having a pore size such that oxygen and other molecules important to cell survival and function can move through the semi-permeable membrane but the cells of the immune system cannot permeate or traverse through the pores. Similarly, such devices can contain therapeutically effective quantities of a biologically active agent, e.g., an angiogenic factor, a growth factor, a hormone and the like.

The devices described herein can be employed for treating pathologies requiring a continuous supply of biologically active substances to the organism. Such devices are, for example, can also be referred to as, bioartificial organs, which contain homogenous or heterogenous mixtures of biologically active agents and/or cells, or cells producing one or more biologically active substances of interest. Ideally, the biologically active agents and/or cells are wholly encapsulated or enclosed in at least one internal space or are encapsulation chambers, which are bounded by at least one or more semi-permeable membranes. Such a semi-permeable membrane should allow the encapsulated biologically active substance of interest to pass (e.g., insulin, glucagon, pancreatic polypeptide and the like), making the active substance available to the target cells outside the device and in the patient's body. In a preferred embodiment, the semi-permeable membrane allows nutrients naturally present in the subject to pass through the membrane to provide essential nutrients to the encapsulated cells. At the same time, such a semi-permeable membrane prohibits or prevents the patient's cells, more particularly to the immune system cells, from passing through and into the device and harming the encapsulated cells in the device. For example, in the case of diabetes, this approach can allow glucose and oxygen to stimulate insulin-producing cells to release insulin as required by the body in real time while preventing immune system cells from recognizing and destroying the implanted cells. In a preferred embodiment, the semi-permeable membrane prohibits the implanted cells from escaping encapsulation.

Preferred devices may have certain characteristics which are desirable but are not limited to one or a combination of the following: i) comprised of a biocompatible material that functions under physiologic conditions, including pH and temperature; examples include, but are not limited to, anisotropic materials, polysulfone (PSF), nano-fiber mats, polyimide, tetrafluoroethylene/polytetrafluoroethylene (PTFE; also known as Teflon®), ePTFE (expanded polytetrafluoroethylene), polyacrylonitrile, polyethersulfone, acrylic resin, cellulose acetate, cellulose nitrate, polyamide, as well as hydroxylpropyl methyl cellulose (HPMC) membranes; ii) releases no toxic compounds harming the biologically active agent and/or cells encapsulated inside the device; iii) promotes secretion or release of a biologically active agent or macromolecule across the device; iv) promotes rapid kinetics of macromolecule diffusion; v) promotes long-term stability of the encapsulated cells; vi) promotes vascularization; vii) comprised of membranes or housing structure that is chemically inert; viii) provides stable mechanical properties; ix) maintains structure/housing integrity (e.g., prevents unintended leakage of toxic or harmful agents and/or cells); x) is refillable and/or flushable; xi) is mechanically expandable; xii) contains no ports or at least one, two, three or more ports; xiii) provides a means for immuno-isolating the transplanted cells from the host tissue; xiv) is easy to fabricate and manufacture; and xv) can be sterilized.

The embodiments of the encapsulation devices described herein are in not intended to be limited to certain device size, shape, design, volume capacity, and/or materials used to make the encapsulation devices, so long as one or more of the above elements are achieved.

Device Designs

In one embodiment, the encapsulated device is improved by creating one or more compartments in the device, other than that created by sealing or welding the device around the periphery or edges to prevent leakage of the cells and/or biologically active agents. FIG. 1 is an example of a schematic of one embodiment of the device, but the device is not intended to be bound to just this design. Rather, the design can include variations such as those routine in the art. In some embodiments, device design can be modified depending on the type of biologically active agents and/or cells encapsulated and to meet the needs and function of the study. A device of any size or shape reasonable can be further compartmentalized into having at least 1, at least 2, at least 3, at least 4, at least 5, at least 6, at least 7, at least 8, at least 9, at least 10, at least 11, at least 12, at least 13, a least 14, at least 15, at least 16, least 17, at least 18, at least 19, at least 20, at least 21, at least 22, at least 23, at least 24 or more chambers or compartments. One purpose for creating a plurality of compartments is that it increases the surface area for nutrient and oxygen exchange between the encapsulated cells and, for example and the interstitial space surrounding the device; see FIGS. 1-11 for example. Further, such designs prohibit or do not promote large cell aggregates or clusters or agglomerations such that cells packed in the center of the large clusters/agglomerations are denied, or receive less, nutrients and oxygen and therefore potentially do not survive. Devices containing a plurality of chambers or compartments therefore are better capable to disperse the cells throughout the chamber/compartment or chambers/compartments. In this way, there is more opportunity for each cell to receive nutrients and oxygen, thereby promoting cell survival and not cell death.

Figure 6:
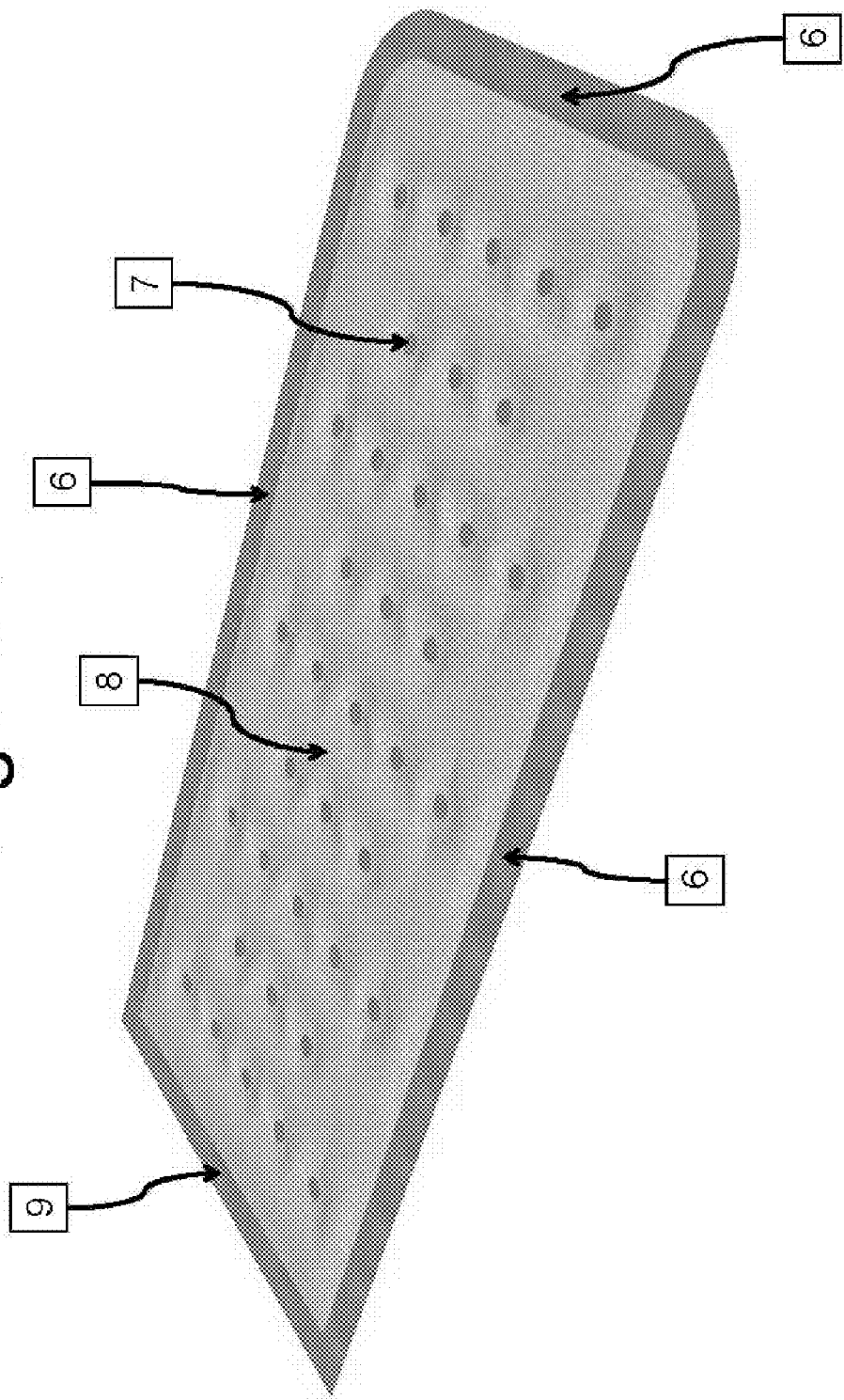
FIG. 6 is a perspective view of an encapsulation device without loading ports and containing periodic ultrasonic spot-welds to compartmentalize the internal lumen.

One embodiment relates to a substantially elliptical to rectangular shape device; see FIGS. 1 and 6. These devices are further compartmentalized or reconfigured so that instead of a slightly flattened device there is a weld or seam running through the center of the device, either sealing off each half of the device, thus forming two separate reservoirs, lumens, chambers, void spaces, containers or compartments; or the weld or seam creates one U-shaped chamber which is separated or divided in the middle due to the weld but such a weld in this instance does not completely seal off the chambers; see FIG. 1. In FIG. 1 two ports provides for ease of filling and flushing cells into and through the chambers.

Another embodiment relates to a similar elliptical or rectangular shape device having 2, 3, 4, 5, 6, 7, 8, 9, 10 or more welds across the plane of the device. In some aspects the welds are across the horizontal aspect or plane of the device. In other aspects the welds are across the vertical aspect or plane of the device. In still other aspects, intersecting welds are present across both the horizontal and vertical aspects of the plane. In some aspects the welds are parallel and equidistant to each other. In other aspects the welds are perpendicular. In still other aspects the welds are parallel but not equidistant. As in the above example, such a design can effectively form up to 2, 3, 4, 5, 6, 7, 8, 9, 10 or more chambers, wholly separated if the weld runs traverses and connects both boundaries of the device, or it can create one continuous chamber but interdigitated. Further, although certain exemplary devices are described in FIGS. 1-11 with welds being parallel or parallel and equidistant, still other devices can be customized or made with welds in any direction or orientation, including long welds which have regions interrupted by no welds. The type and number of welds used can depend on the cell population or agent employed and for what treatment or purpose. In some embodiments, welds can be arranged to modify the look of the device.

FIG. 1 shows an encapsulation device that embodies features described herein, but as described above, this is just one illustration and one of ordinary skill in the art can envisage that by forming different configurations using welds or seams in any such device, one can customize the number of compartments suitable for the purpose. FIGS. 2-5 show top, side and end cross sections of the same device. The device can be ultrasonically welded around the entire perimeter 1 to create a completely enclosed internal lumen. Other means of sealing or walling off membranes to form the pouch like device can be used. The lumen is further compartmentalized by an internal weld 2 that is centrally located and extends down the long axis of the device. This weld extends to a point 3 that effectively limits the thickness or depth of each compartment yet does not completely segregate the internal lumen. By this approach, the width and depth of the compartments are controlled and can be varied as is required to enable cell product survival and performance. Moreover, all dimensions of the device, which include but are not limited to, the overall length, overall width, perimeter weld thickness, perimeter weld width, compartment length, compartment width, compartment depth, internal weld length, internal weld width and port position are design specifications that can be modified to optimize the device for unique cell products and/or biologically active agents.

Referring to FIG. 1, the compartment is loaded with a cell product or biologically active agent through two individual ports 5, 5' that are incorporated into the device during ultrasonic welding of the perimeter. These ports extend into the lumen or compartments and allow access to the compartment for the purpose of evenly distributing cells and/or agents during loading. Further, as the ports 5,5' are connected via the U-shaped internal lumen as in FIG. 1, gas is allowed to vent through each port 5 while the adjacent port 5' is being loaded, thus preventing the accumulation of pressure in the device.

Figure 7:
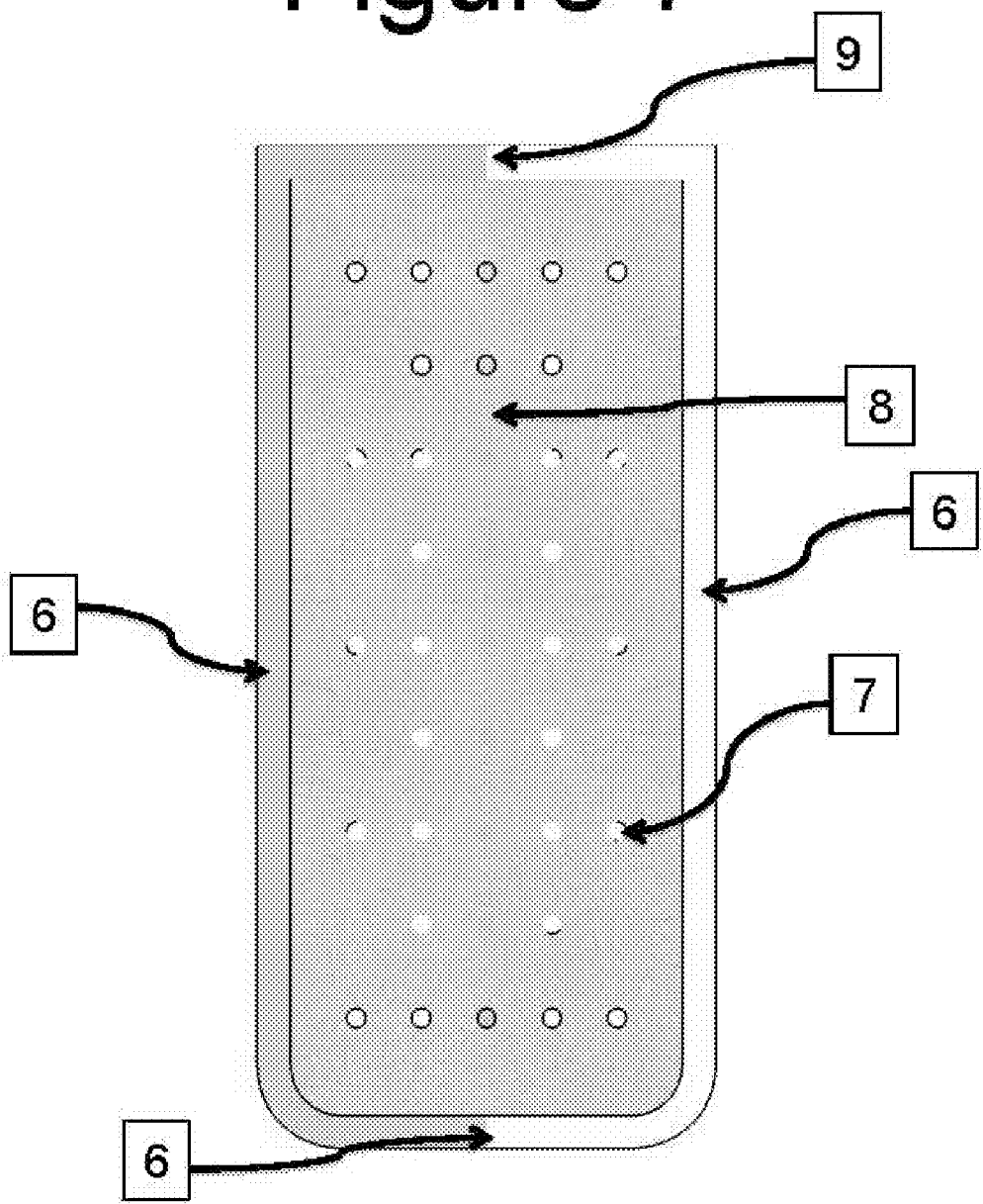
FIG. 7 is a top cross section view of the encapsulation device shown in FIG. 6
Figure 8:
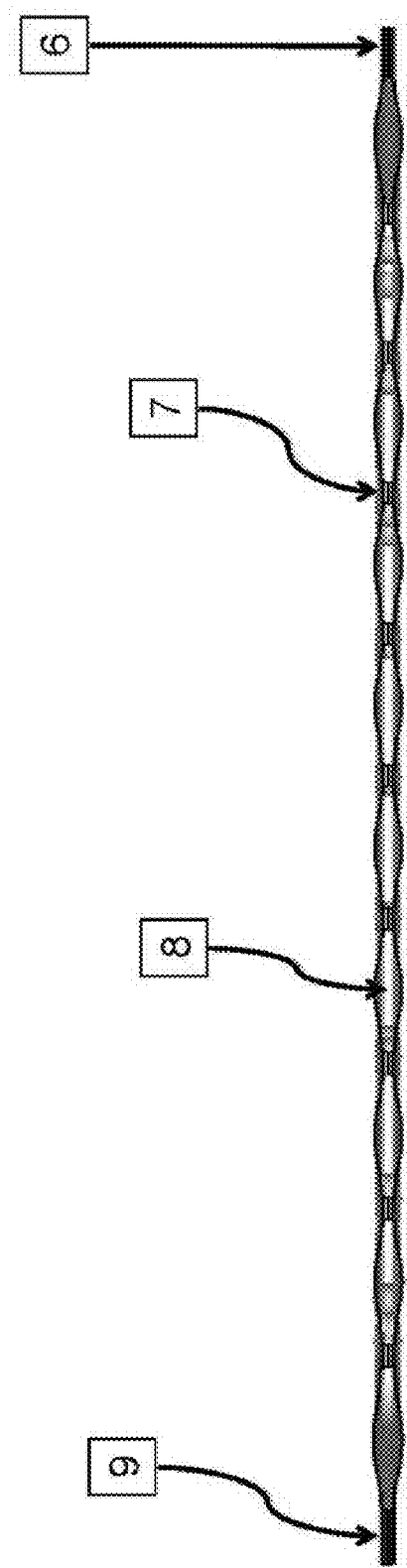
FIG. 8 is a side view of the encapsulation device shown in FIG. 6 with a cross section taken through the center of a compartmentalized lumen.
Figure 9:
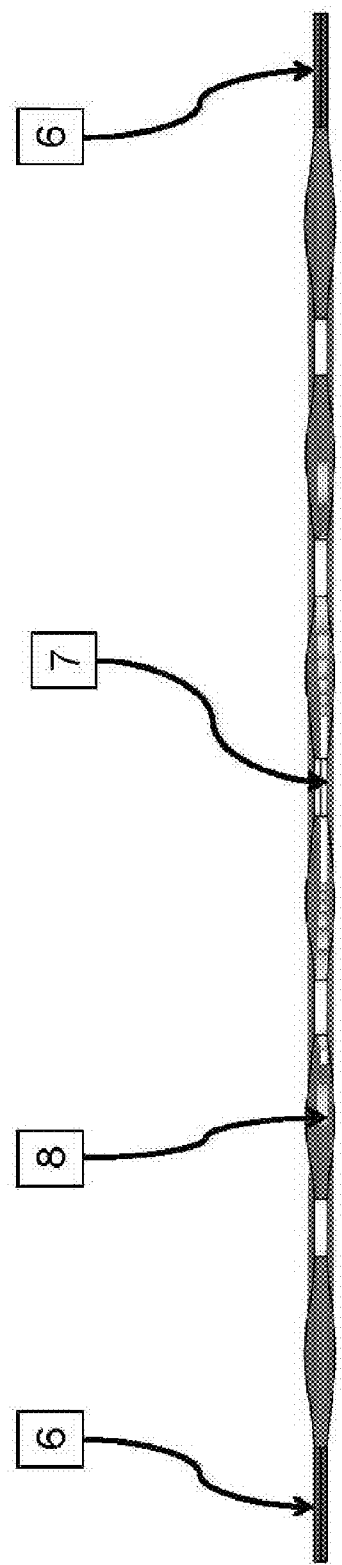
FIG. 9 is an end view of the encapsulation device shown in FIG. 6 with a cross section through the compartmentalized lumens.

Alternatively, in another embodiment, the devices provided herein contain no ports of entry or exit, i.e. the devices are said to be port-less. Such an embodiment is shown in FIG. 6. FIGS. 7-9 show a top, side and end cross section of a substantially similar device. A two, three or more stage welding process may be necessary to create a port-less device as that shown in FIGS. 6-11. For example, in one aspect, the elliptical/rectangular outer perimeter 6 and the compartmentalization spot welds 7 are first created by ultrasonic welding. The spot welds 7 function similarly to the internal weld 2 of FIG. 1. The spot welds 7 are placed is a manner across the device to periodically limit the expansion of the lumen or compartment 8 at any given point. Again, the lumen or compartments 8 created by spot welding, therefore interconnecting the compartments 8, and not isolating or wholly separating any one lumen or compartment. Moreover, the total number, diameter and distribution of the spot welds 7 are design parameters that can be optimized to accommodate the loading dynamics and growth rates of any cell product or agent.

Once cells are loaded into the device, the outer perimeter is completely and aseptically sealed by a second ultrasonic weld across the edge 9 of the device. The result of the multi-step sealing process is that finished devices are totally enclosed and have no ports extending from the perimeter. This approach simplifies the loading process and improves the overall integrity and safety of the device, as the ports can be an area of the perimeter where breaches can occur as a result of suboptimal ultrasonic welding.

Further, although the above process was described in 2 sequential steps, the means for encapsulating the cells and/or agents is not limited to the described 2 steps but to any number of steps, in any order, necessary to encapsulate the cells and at the same time prevent or reduce the level of breach of the device.

Figure 10:
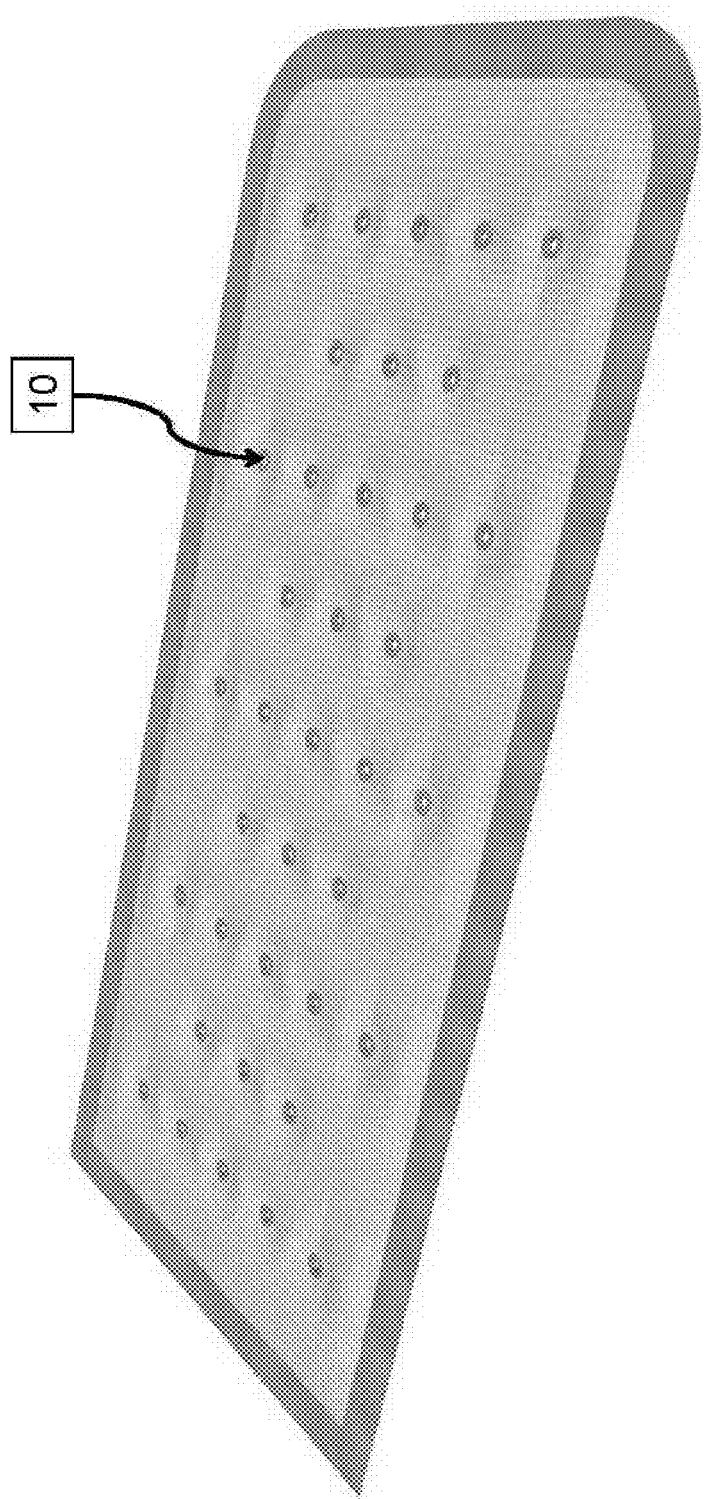
FIG. 10 is a perspective view of an encapsulation device without loading ports and containing periodic ultrasonic spot-welds to compartmentalize the internal lumen. Each of the spot welds has the center removed to facilitate vascularization.
Figure 11:
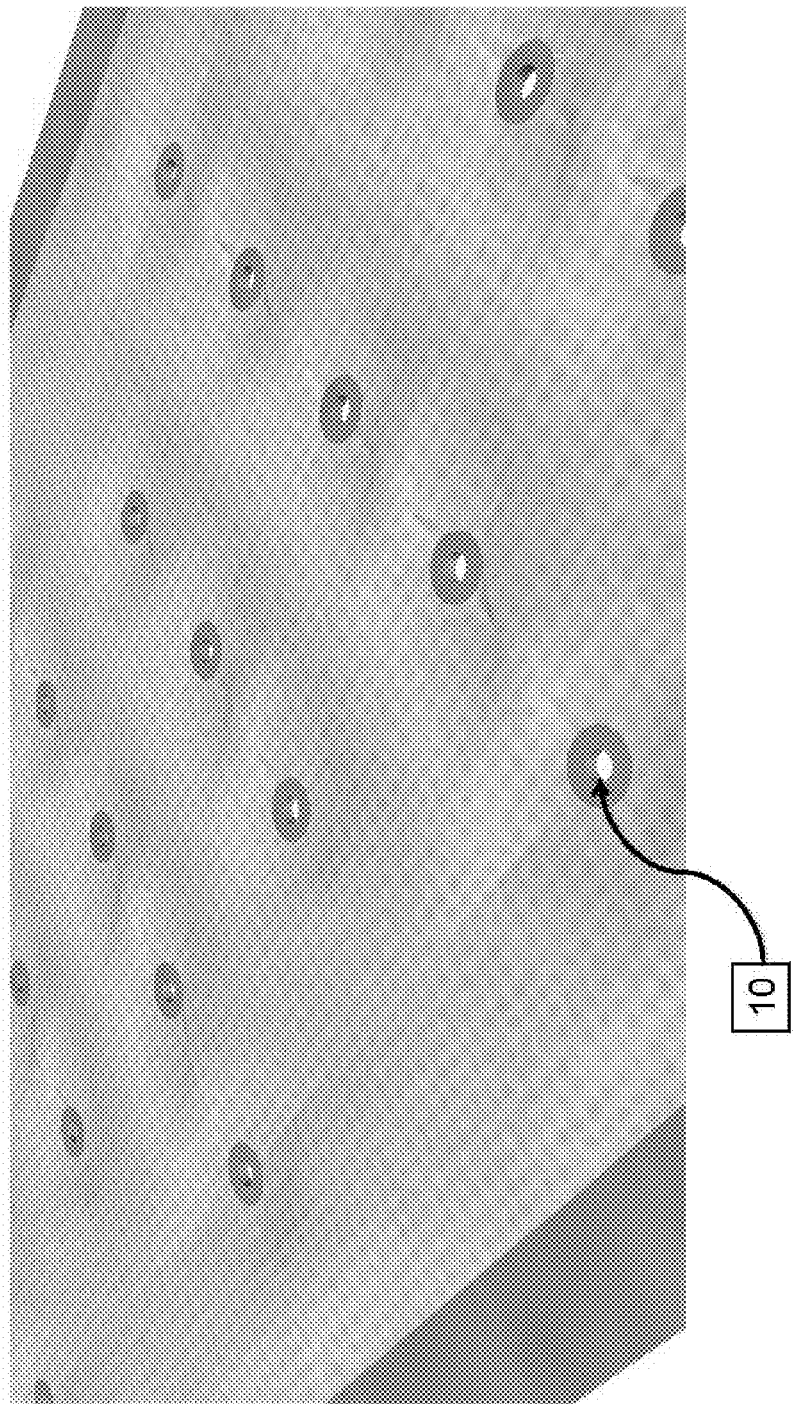
FIG. 11 is an enlarged view of the encapsulation device shown in FIG. 10.

In another embodiment, FIGS. 10 and 11 show an encapsulation device substantially similar to the device shown in FIG. 6, but the spot welds 10 have been modified during the welding process to have the centers removed. One of ordinary skill in the art cam accomplish this in various ways, e.g., by using an ultrasonic sonotrode that has an internal sharpened edge, which can cut the material immediately after welding. These cut-out welds 10 have an advantage in that they are more readily integrated with the host tissue because the cut-out welds 10 promote vascularization of the device, thus improving the survival and performance of oxygen-dependent cell products and/or agents. As a consequence of facilitating and promoting new vasculature through the device, there is improved diffusive transport of oxygen in the X-Y direction, which is normally limited towards the center of planar sheet devices.

In other embodiments, the device design can be different shapes, e.g. the cell encapsulation device can be in the shape of a tube or flattened tube or any other such shape which satisfies one of the above requirements for a device of the invention.

Device Materials

Cell permeable and impermeable membranes comprising of have been described in the art including those patents previously described above by Baxter or otherwise previously referred to as TheraCyte cell encapsulation devices including, U.S. Pat. Nos. 6,773,458; 6,520,997; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518; 5,219,361; 5,100,392; and 5,011,494, which are herein incorporated by reference in their entireties.

In one embodiment, the encapsulating devices are comprised of a biocompatible material including, but are not limited to, anisotropic materials, polysulfone (PSF), nanofiber mats, polyimide, tetrafluoroethylene/polytetrafluoroethylene (PTFE; also known as Teflon®), ePTFE (expanded polytetrafluoroethylene), polyacrylonitrile, polyethersulfone, acrylic resin, cellulose acetate, cellulose nitrate, polyamide, as well as hydroxylpropyl methyl cellulose (HPMC) membranes. These and substantially similar membrane types and components are manufactured by at least Gore®, Phillips Scientific®, Zeus®, Pall® and Dewal® to name a few.

Immobilized Device

Also provided is an implantable device, which is immobilized at an implantation site to maintain the encapsulated cell and/or biological active agent at the implantation site and permit diffusion of, for example, an expressed and secreted therapeutic polypeptide from the implantation site. In one aspect, the implantation site is at, or close in proximity to, the tissue or organ which is focus of the treatment. In other aspects, where delivery of the secreted agent from the device is not location dependent and biodistribution of the agent is dependent on the vasculature, the device can be implanted in a remote location. For example, in a preferred embodiment, the biocompatible device is implanted subcutaneously under the skin on the forearm, or flank, or back, or buttocks, or leg and the like, where it substantially remains until such time as it is required for it to be removed.

Expandable Devices

Devices described herein have inner and outer surfaces wherein the device contains at least one void (or reservoir, or lumen, or container or compartment) and wherein at least one void is open to the inner surface of the device. Conventional implantable devices are commonly made of rigid, non-expandable biocompatible materials. One embodiment of the device described herein is made of an expandable material. Other embodiments are directed to non-expandable materials. Whether the device is capable of expanding may be an inherent part of the materials employed to make the device, e.g., a polymer sheath which is expandable, or can be designed such that they are expandable or have expandable capabilities. For example, a device which expands in size to house additional cells or to refill an existing device is provided.

In another embodiment, the implantable device is contained in a housing or holder, which is slightly more rigid, and non-expandable but allowing sufficient means to increase cell or agent capacity by increasing the number of or implant devices. For example, means for inserting an additional reservoir, lumen, container, compartment or cassette each having pre-loaded cells or agent. Alternatively, the housing contains a plurality of devices only some of which are loaded with cells or have cells encapsulated therein, while others are empty, which can be loaded and filled with cells or agents at a later period in time or any time subsequent the initial implantation. Such an expandable housing is comprised of inert materials suitable for implantation in the body, e.g., metal, titanium, titanium alloy or a stainless steel alloy, plastic, and ceramic appropriate for implantation in the mammal, more specifically, the human body.

Still in another embodiment, such a housing or implant device holder includes an outer sleeve having a longitudinal axis, at least one passage along the longitudinal axis, and a distal end and a device engagement area adapted to cooperatively engage the device. As an analogy, the device holder functions similarly to a disk or cassette holder capable of housing more than one disk or cassette at any one time or for a long period of time. In still another embodiment, the device holder contains an expander adapted to increase the height of the holder Refillable Cell Encapsulation Devices Another embodiment relates to an encapsulation device with a refillable reservoir, lumen, container or compartment, which can be periodically filled or flushed with appropriate therapeutic or biologically active agents and/or cells. Such filling may be accomplished by injecting a therapeutically effective amount of the appropriate therapeutic or biologically active agents and/or cells into an implanted reservoir, lumen, container or compartment, e.g., subdermally or subcutaneously using a syringe or other standard means in the art for filling like reservoirs, lumens, containers or compartments in vivo.

Encapsulated Cells

In some embodiments, the system comprises a cell density between about $1\times10^5$, $1\times10^6$ cells/ml to about $1\times10^{10}$ cells/mL or more. In some embodiments, the cell survives under culture conditions or in vivo in the system for at least a month, two months, three months, four months, five months, six months, seven months, eight months, nine months, ten months, eleven months, twelve months or a year or more with a functionality that represents at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more of the function expressed at the time the cells are/were introduced into the system or at the time the cells fully develop and/or mature in the system, e.g. implantation of progenitor cells which need to further develop or mature to functional cells in vivo. In some embodiments, the cell in the system expands in said system to increase in cell density and/or cell function upon implantation of the system in vivo.

Methods for Increasing Cell Viability

One obstacle to the field of cell and tissue encapsulation/immuno-isolation has been the lack of sufficient oxygen and nutrient transport across the polymer membranes used to encapsulate cells and tissues. The result of this insufficient gas and nutrient exchange is lowered metabolic activity and cell death. Embodiments described herein relate to an implantable cell encapsulation device addressing this drawback of the prior art.

Oxygen partial pressures have been measured within islets, in their native environment, after isolation, and post-transplant in various polymer devices as well as naked or free, for example, under the kidney capsule. Oxygen partial pressures in pancreatic islets are the highest of any organ in the body (37-46 mmHg). However, upon isolation, these values fall drastically (14-19 mm Hg). Upon transplantation of pancreatic islets into normo-glycemic animals the values decrease slightly (9-15 mmHg) as compare to their isolated values. See Dionne et al., Trans. Am. Soc. Artf. Intern. Organs. 1989; 35: 739-741; and Carlsson et al., Diabetes July 1998 47(7):1027-32, the disclosure of which is herein expressly incorporated by reference. These studies demonstrate that when tissues are immuno-isolated and transplanted, even in a vascularized region such as the kidney capsule, the oxygen partial pressures drop as compared to their native states (37-46 mmHg). Hence, these nearly anoxic conditions can result in cell death, particularly the nearer the cell to the core of a cell cluster or core of an encapsulating device.

In order to achieve better oxygen availability and delivery to the encapsulated cells or tissues and/or biologically active agents, embodiments described herein relate to the use of, for example, perfluorinated substances in the device design and/or formulation, e.g., in the membranes or materials employed for assembly of the device. In particular, perfluoro organic compounds, e.g., perfluorocarbons (PFCs), are good solvents because they have several fold higher solubility for oxygen than water. For example, under normal conditions, liquid PFCs dissolve between 40 and 55% by volume of oxygen and between 100 and 150% by volume of CO2. PFCs are largely used as blood substitutes and tissue preservation. Additionally, PFC derivatives are dense, chemically inert, and water insoluble compounds that cannot be metabolized.

In another aspect of the embodiments, enhanced $O_2$ delivery is performed by a PFC-emulsion or mixture of PFC with some matrix. The device components or cells for example could be suspended or soaked or incubated in the emulsion/matrix to form a coating. Still certain PFC emulsions with higher weight/volume concentrations have been known to have improved oxygen delivery and retention properties. And because of the higher oxygen partial pressure created by the $O_2$ carrying capabilities of PFCs, an $O_2$ pressure gradient is created that drives diffusion of dissolved oxygen into the tissue, thereby enhancing $O_2$ delivery to the cells.

The PFC substance includes but is not limited to perfluorotributylamine (FC-43), perfluorodecalin, perfluorooctyl bromide, bis-perfluorobutyl-ethene, or other suitable PFCs. Preferred PFCs typically contain about 60 to about 76 weight percent carbon-bonded fluorine. The perfluorinated fluids can be single compounds, but usually will be a mixture of such compounds. U.S. Pat. No. 2,500,388 (Simons); U.S. Pat. No. 2,519,983 (Simons); U.S. Pat. No. 2,594,272 (Kauck et al.); U.S. Pat. No. 2,616,927 (Kauck et al.); and U.S. Pat. No. 4,788,339 (Moore et al.), the disclosures of which are herein incorporated by reference in their entireties. PFCs useful in the embodiments described herein also include those described in Encyclopedia of Chemical Technology, Kirk-Othmer, Third Ed., Vol. 10, pages 874-81, John Wiley & Sons (1980). For example, useful PFCs include perfluoro-4-methylmorpholine, perfluorotriethylamine, perfluoro-2-ethyltetrahydrofuran, perfluoro-2-butyltetrahydrofuran, perfluoropentane, perfluoro-2-methylpentane, perfluorohexane, perfluoro-4-isopropylmorpholine, perfluorodibutyl ether, perfluoroheptane, perfluorooctane, and mixtures thereof. Preferred inert fluorochemical liquids include perfluorohexane, perfluoro-2-butyltetrahydrofuran, perfluoroheptane, perfluorooctane, and mixtures thereof. Commercially available PFCs useful in the embodiments described herein include FLUORINERT™ fluids, e.g., FC-72, FC-75, FC-77 and FC-84, described in the 1990 product bulletin #98-0211-5347-7(101.5) NPI, FLUORINERT™ fluids, (available from Minnesota Mining and Manufacturing Company, St. Paul, Minn.), and mixtures thereof.

In Vivo Imaging Capability

In one embodiment, there is provided a means for imaging or detecting the cells inside the encapsulating devices in vivo. Imaging serves important roles in stem cell therapies. For example, noninvasive forms of imaging can be used to: (1) determine the presence, severity or phenotype of the cell and/or disease to be treated; (2) monitor engrafted cell therapies for the appearance of deleterious or non-target cell types and structures, such as cysts or microcysts; (3) guide the delivery of therapy; (4) follow the time-course of disease and evaluate the effects or efficacy of therapy; (5) provide labels and define mechanisms of therapy; (6) analyze and evaluate survival and function of engrafted cells; and (7) generally facilitate the process of any cell therapy, e.g. by determining the engraftment, survival, and local function of cell therapy, including cell therapies described herein for treatment of diabetes by substitution and/or implanting pancreatic progenitor cells. In addition, although cell therapies aim to decrease morbidity/mortality, noninvasive imaging techniques as described herein and in more detail below can serve as a useful surrogate endpoint, for example, in preliminary trials or preclinical studies.

Any in vivo imaging technology is ideally: i) non-invasive; ii) reliably repetitive; iii) capable of tissue penetration up to a depth of at least 3 mm; iv) resolution capabilities of no greater than 100 μm and ideally no greater than 50 μm; v) imaging is not attenuated by device materials, e.g., can image through PTFE; vi) clinically compatible and not technically cumbersome or complicated; vii) commercially available; viii) FDA approved for human use; ix) reasonably cost-effective; and x) can image cells in a reasonable period of time (e.g., seconds or minutes), or any combination of the above.

To date, current methods include but are not limited to confocal microscopy, 2-photon microscopy, high frequency ultrasound, optical coherence tomography (OCT), photoacoustic tomography (PAT), computed tomography (CT), magnetic resonance imaging (MRI), single photon emission computed tomography (SPECT) and positron emission tomography (PET). These alone or combined can provide useful means to monitor the transplanted cells. Also, it is expected that such technologies will improve over time but that the essential tenets of how each technology functions or its utility is substantially similar. That said, in vivo imaging described herein is not intended to be limited to technologies described below but to technologies later discovered and described which would serve the same utility as that described herein.

In one embodiment, the imaging technique employed would be non-invasive and provide for a 3-dimensional tomographic data, have high temporal and spatial resolution, allow molecular imaging, and would be inexpensive and portable. While at present no single modality is ideal (discussed in more detail below), each has different attributes and these modalities together can provide complimentary information.

Confocal microscopy is an optical imaging technique that increases micrograph contrast and is capable of reconstructing three-dimensional images by using a spatial pinhole to eliminate out-of-focus light in specimens that are thicker than the focal plane. Since only one point in the sample is illuminated at a time, 2D or 3D imaging requires scanning over a regular raster (i.e. a rectangular pattern of parallel scanning lines) in the specimen. Three principal scanning variations are commonly employed to produce confocal microscope images. Fundamentally equivalent confocal operation can be achieved by employing a laterally translating specimen stage coupled to a stationary illuminating light beam (stage scanning), a scanned light beam with a stationary stage (beam scanning), or by maintaining both the stage and light source stationary while scanning the specimen with an array of light points transmitted through apertures in a spinning Nipkow or Nipkov disk. Each technique has performance features that make it advantageous for specific confocal applications, but that limits the usefulness of that feature for other applications.

All confocal microscopes rely on the ability of the technique to produce high-resolution images, termed optical sections, in sequence through relatively thick sections or whole-mount specimens. Based on the optical section as the basic image unit, data can be collected from fixed and stained specimens in single, double, triple, or multiple-wavelength illumination modes, and the images collected with the various illumination and labeling strategies will be in register with each other. Live cell imaging and time-lapse sequences are possible, and digital image processing methods applied to sequences of images allow z-series and three-dimensional representation of specimens, as well as the time-sequence presentation of 3D data as four-dimensional imaging. The use of above confocal microscopes is not limiting as other confocal microscopes now or later discovered are also encompassed in the embodiments described herein.

A large number of fluorescent probes are available that, when incorporated in relatively simple protocols, can stain certain cellular surface markers and/or proteins and intracellular organelles and structures, e.g., Celltracker, DiI, nuclear vital dyes, and the like. Fluorescent markers which specifically bind directly or indirectly to certain cell surface markers can be especially useful for identification of for example unwanted cell types. In one preferred embodiment, real time in vivo imaging for the presence of encapsulated pluripotent cells provides a means to detect, and therefore the potential to prevent, teratoma formation caused from pluripotent stem cells, such as hES or human embryonic gonadal cells or induced pluripotent stem (IPS) cells or parthenote cells and the like. The same means of detection can also identify pluripotent Stem cells which have escaped or leaked out of the device (or become un-encapsulated). Identification of such cells can also be performed using fluorescently labeled promoter genes OCT4 and NANOG that are up-regulated in expression in pluripotent stem cells. Similarly, certain intracellular fluorescent markers that label nuclei, the Golgi apparatus, the endoplasmic reticulum, and mitochondria, and even dyes such as fluorescently labeled phalloidins that target polymerized actin in cells, are also commercially available and can provide critical information about the fate of a cell.

In another embodiment, two-photon excited fluorescence (TPEF) microscopy is a noninvasive means to monitor differentiation or, stated in the reverse, to identify pluripotent stem cells (e.g., hESCs or IPS cells or parthenote cells) which did not differentiate and were inadvertently implanted as a very small percentage of the product cells that were encapsulated in the device described herein. Two-photon excited fluorescence microscopy relies substantially on endogenous sources of contrast, but can also detect, for example, fibrillar matrix molecules via second harmonic generation. In brief, two-photon microscopy relies on fluorescence emission similar to that employed by confocal microscopy. Rice et al. (2007) described that TPEF can be used to reveal quantitative differences in the biochemical status and the shape of differentiating and nondifferentiating stem cells in two-dimensional (2-D). See Rice et al. (2007) J Biomed Opt. 2007 Nov.-Dec.; 12(6), the disclosure of which is expressly incorporated by reference herein. In one embodiment, pluripotent stem cells can be genetically modified to express a fluorescent protein, e.g., enhanced green fluorescent protein, and driven by a pluripotent stem cell promoter (e.g., OCT4 or NANOG or any other pluripotent stem cell promoter later identified). For those implantable devices that are deeper than subcutaneous implants, i.e. deep below the skin surface, two-photon provides for a non-invasive deeper imaging than confocal microscopy. Further, the infrared light used is less harmful to living cells than visible or ultraviolet exposure, as the photon energy required for fluorescence excitation only occurs at the plane of focus and is not experienced by cells or tissues in the out-of-focus planes.

In still another embodiment, ultrasound is portable, essentially harmless, versatile, and can be done in real-time at the time of implantation of the encapsulated cell product and/or encapsulated biologically active agent. In particular, high frequency ultrasound such as that described by VisualSonics. High-resolution imaging enables in vivo assessment of anatomical structures and hemodynamic function in longitudinal studies of mammal. For example, Vevo by VisualSonics offers: (1) ability to perform longitudinal studies of disease progression and regression in individual subjects; (2) image resolution of anatomical and physiological structures of down to 30 microns; (3) ability to visualize image-guided needle injection and extraction; (4) microcirculatory and cardiovascular blood flow assessment; (5) high throughput via user-friendly equipment and research-driven interface; and (6) open architecture allowing comprehensive measurement and annotations and offline data analysis. The ability to assess microcirculatory and cardiovascular blood flow will assist in determining the viability of the cells, e.g. $O_2$ flow and delivery.

In another embodiment, magnetic resonance imaging (MRI) can be utilized to distinguish between healthy and diseased tissue using a contrast agent. Yet, in another embodiment, computerized tomography (CT) or CT scans can be used to create a detailed picture of the body's tissues and structure. Again here, a contrast agent is utilized and makes it easy to visualize abnormal tissue due to specific absorption rates. One use of a contrast agent such as Indium-111 (I-111) oxine is for tracking stem cells although it does have a short half-life. Still, in another embodiment, Positron Emission Tomography (PET) scans can be used to measure emissions from positron-emitting molecules e.g., carbon, nitrogen, and oxygen to name a few, and provide valuable functional information. In yet another embodiment, optical coherence tomography (OCT) or photoacoustic tomography (PAT) may also be used to examine cells and tissues inside and outside the device. OCT detects differences in the reflectivity of various tissues while PAT detects ultrasonic waves created when tissues are heated by exposure to low energy laser light.

Various methods and techniques or tools, alone or combined, can be employed to visualize, analyze and assess the implanted cells inside the device in vivo. These and other technologies now known or later developed can be utilized to the extent they allow for in vivo imaging and monitoring of the cells and/or agent as described herein.

Throughout this application, various publications are referenced. The disclosures of all of these publications and those references cited within those publications in their entireties are hereby incorporated by reference into this application in their entirety in order to more fully describe the state of the art to which this patent pertains.

EXAMPLE 1

Encapsulated Pancreatic Progenitors Function In Vivo

The following example was performed, at least in part, to first determine the integrity of methods of encapsulating pancreatic progenitor cells, including a bio-compatible device and a medical/mechanical device; and second to determine whether wholly encapsulated pancreatic progenitor cells survive and mature to functioning hormone-secreting cells in vivo as compared to unencapsulated pancreatic progenitor cells (controls).

Methods for producing pancreatic cell lineages from human embryonic stem (hES) cells are substantially as described in U.S. Pat. No. 7,534,608, entitled METHODS OF PRODUCING PANCREATIC HORMONES, U.S. application Ser. No. 12/264,760, entitled STEM CELL AGGREGATE SUSPENSION COMPOSITIONS AND METHODS OF DIFFERENTIATION THEREOF, filed Oct. 4, 2008; U.S. application Ser. No. 11/773,944, entitled METHODS OF PRODUCING PANCREATIC HORMONES, filed Jul. 5, 2007; U.S. application Ser. No. 12/132,437, GROWTH FACTORS FOR PRODUCTION OF DEFINITIVE ENDODERM, filed Jun. 3, 2008; U.S. application Ser. No. 12/107,020, entitled METHODS FOR PURIFYING ENDODERM AND PANCREATIC ENDODERM CELLS DERIVED FROM HUMAN EMBRYONIC STEM CELLS, filed Apr. 8, 2008; U.S. application Ser. No. 11/875,057, entitled METHODS AND COMPOSITIONS FOR FEEDER-FREE PLURIPOTENT STEM CELL MEDIA CONTAINING HUMAN SERUM, filed Oct. 19, 2007; U.S. application Ser. No. 11/678,487, entitled COMPOSITIONS AND METHODS FOR CULTURING DIFFERENTIAL CELLS, filed Feb. 23, 2007; U.S. Pat. No. 7,432,104, entitled ALTERNATIVE COMPOSITIONS & METHODS FOR THE CULTURE OF STEM CELLS; Kroon et al. (2008) Nature Biotechnology 26(4): 443-452; d'Amour et al. 2005 Nat. Biotechnol. 23:1534-41; D'Amour et al. 2006 Nat. Biotechnol. 24(11): 1392-401; McLean et al., 2007 Stem Cells 25:29-38, which are all herein incorporated in their entireties by reference.

Briefly, undifferentiated human embryonic stem (hES) cells were maintained on mouse embryo fibroblasts feeder layers (Specialty Media) in DMEM/F12 (Mediatech) supplemented with 20% KnockOut serum replacement (KOSR, GIBCO BRL), 1 mM nonessential amino acids (GIBCO BRL), Glutamax (GIBCO BRL), penicillin/streptomycin (GIBCO BRL), 0.55 mM of 2-mercaptoethanol (GIBCO BRL) and 4 ng/mL recombinant human FGF2 (R&D Systems) and alternatively supplemented in 10-20 ng/mL of Activin A (R&D Systems). Human ES cell cultures were manually passaged at about 1:4 to 1:8, 1:9, or 1:10 split ratio every 5 to 7 days. Prior to differentiation either as adherent cultures or in cell aggregate suspensions, they were given a brief wash in $PBS^{+/+}$ (containing $Mg^{++}$ and $Ca^{++}$, Invitrogen). Human ES cell lines can include, but are not limited to, CyT49, CyT203, Cyt25, BG01 and BG02.

Methods for culturing and differentiating cells or cell populations in suspension are described in detail in International Application PCT/US2007/062755, COMPOSITIONS AND METHODS FOR CULTURING DIFFERENTIAL CELLS, filed 23 Feb. 2007 and U.S. application Ser. No. 12/264,760, STEM CELL AGGREGATE SUSPENSION COMPOSITIONS AND METHODS OF DIFFERENTIATION THEREOF, filed 4 Nov. 2008, which are herein incorporated by reference in their entireties.

The differentiation culture conditions were substantially similar to that described in D'Amour et al. 2006, supra, and Example 4 below, both describing a 5 step differentiation protocol: stage 1 (definitive endoderm; d 1-d 4), stage 2 (primitive gut tube or foregut endoderm; d 5 to d 8), stage 3 (posterior foregut or Pdx1-positive endoderm; d 9 to d 12), stage 4 (pancreatic progenitor, pancreatic epithelium and/or endocrine precursor; d 13 to d 15) and stage 5 (hormone expressing endocrine cell, d 16 or more).

At stage 4, retinoic acid (RA) was withdrawn from the stage 3 cultures, the cultures were washed once with DMEM plus B27 (1:100 Gibco), and then the wash was replaced with either DMEM+1XB27 supplement alone or with any combinations of or any or all of the following factors: Noggin (50 ng/ml), FGF10 (50 ng/ml), KGF (25-50 ng/ml), EGF (25-50 ng/ml), 1-5% FBS for 4-8 days. In cases where no RA was added, noggin at 30-100 ng/mL (R&D systems) was added to the media for 1-9 days. Alternatively, no additional growth factors were added at stage 4. Also, cell-survival agents such as Y-27632, fasudil, H-1152P, and a mixture comprising insulin/transferrin/selenium (ITS) can be added to the cultures.

Regardless of whether the pancreatic progenitors were produced from adherent cultures or in cell aggregate suspensions, all pancreatic progenitor cell populations when transplanted in mammals developed and matured into functional endocrine tissues in vivo. In vivo production of insulin by the hES-derived transplanted cells is described in the U.S. Applications and references above, e.g., U.S. application Ser. No. 11/773,944, entitled METHODS OF PRODUCING PANCREATIC HORMONES and Kroon et al. 2008, supra.

Unlike the cell compositions described in U.S. application Ser. No. 11/773,944 and Kroon et al. 2008 supra, the pancreatic progenitors in this study were wholly isolated or encapsulated in vivo. Pancreatic progenitor cells were encapsulated using a bio-compatible polyethylene glycol (PEG), which is described in more detail in U.S. Pat. No. 7,427,415, entitled IMPLANTATION OF ENCAPSULATED BIOLOGICAL MATERIALS FOR TREATING DISEASES, which is herein incorporated by reference. PEG-encapsulated pancreatic progenitors were transplanted under the epididymal fat pad (EFP); serum C-peptide levels at various time points post glucose-stimulation were determined; and immunohistochemical analysis was done on the PEG-encapsulated explants. Again, these methods have been previously described in U.S. application Ser. No. 11/773,944, entitled METHODS OF PRODUCING PANCREATIC HORMONES and Kroon et al. 2008, supra. (data not shown). Immunohistochemical analysis showed that the pancreatic progenitor cells were capable of maturing in vivo and contained hormone expressing cells such as insulin, glucagon and somatostatin.

Encapsulation of the pancreatic progenitor cells was also performed using a medical or mechanical device, e.g., a TheraCyte cell encapsulation device. All references to Thera-Cyte cell encapsulation devices are to devices that were purchased directly from the manufacturer (Theracyte, Inc., Irvine, Calif.) and are further described in U.S. Pat. Nos. 6,773, 458; 6,156,305; 6,060,640; 5,964,804; 5,964,261; 5,882,354; 5,807,406; 5,800,529; 5,782,912; 5,741,330; 5,733,336; 5,713,888; 5,653,756; 5,593,440; 5,569,462; 5,549,675; 5,545,223; 5,453,278; 5,421,923; 5,344,454; 5,314,471; 5,324,518; 5,219,361; 5,100,392; and 5,011,494, which are all herein incorporated in their entireties by reference. Pancreatic progenitor cells were either loaded into the devices ex vivo, or once the devices had been implanted for a period of time to allow for prevascularization of the device, then the cells were loaded in vivo via the loading port on one side of the device.

Therefore, the device contains a first membrane which is impermeable to cells (0.4 microns) but at the same does not restrict movement of oxygen and various nutrients in and out of the inner membrane, e.g. glucose from outside the inner membrane can permeate into the capsule containing the mature pancreatic hormone secreting cells, which in response to the glucose, can secrete insulin which then permeates out of the inner membrane. The device also contains an outer vascularizing membrane.

In order to use a device for any cell therapy, the device has to wholly contain the cells in vivo (e.g., immuno-isolate the hES-derived cells from the host). To determine the integrity of the TheraCyte device, intact devices containing the pancreatic progenitor cells were compared to those devices which had perforated holes in the membranes in vivo. Perforating holes into the devices allows for host cellular invasion and therefore establish host-graft cell-to-cell contact.

Two 4.5 μL TheraCyte devices were first prevascularized by surgically implanting them under the epididymal fat pads (EFP) or subcutaneously (SQ) in each male severe combined immunodeficient (SCID)-beige (Bg) mice. That is, one animal received 2 devices under the EFP, and another animal received 2 devices SQ. These intact but empty (no pancreatic progenitor cells) devices remained in the animal for a sufficient period of time allowing for host vasculature structures to form and associate with the device, e.g., at least 2 to 8 weeks. After 8 weeks, about $1.5 \times 10^6$ cells pancreatic progenitor cells derived from hES cells were loaded into each of the 4 devices. At the same time as the animals with the prevascularized devices were being loaded, 3 other animals were implanted with two modified Theracyte devices wherein an original Theracyte device of the same size (4.5 μL) was modified with perforations in the membranes of the device. These perforated devices (2 perforated devices per animal) were loaded with cells ex vivo with about the same dosage of cells as was loaded into of the perforated devices. Also at the same time, two positive controls were carried along side these experiments and both animals were grafted with pancreatic progenitors on Gelfoam as described in U.S. application Ser. No. 11/773,944, entitled METHODS OF PRODUCING PANCREATIC HORMONES and Kroon et al. 2008, supra, although in one animal two grafts were placed under the EFP and in the other animal only one graft was placed in the EFP. Table 1 summarizes the results of the above experiments.

TABLE 1

Human C-peptide serum levels from encapsulated mature pancreatic hormone-secreting cells

| Implant | Animal # | 9 week | | 12 week | | 15 week | |
|---|---|---|---|---|---|---|---|
| | | GSIS Time (min) | Human C-pep pM | GSIS Time | Human C-pep pM | GSIS Time | Human C-pep pM |
| PV EFP 2 × 1.5M | 675 | 0 | 91 | 0 | 186 | | |
| | | 60 | 224 | 30 | 304 | | |
| | | | | 60 | 419 | | |
| PV SQ 2 × 1.5M | 676 | 0 | 157 | 0 | 322 | 0 | 908 |
| | | 60 | 610 | 30 | 532 | 5 | 874 |
| | | | | 60 | 2637 | 30 | 3037 |
| nPV + holes EFP 2 × 1.5M | 679 | 0 | 239 | 0 | 374 | | |
| | | 60 | 727 | 30 | 482 | | |
| | | | | 60 | 2259 | | |
| | 680 | 0 | 218 | 0 | 329 | | |
| | | 60 | 899 | 30 | 506 | | |
| | | | | 60 | 2177 | | |
| | 681 | 0 | 408 | 0 | 422 | 0 | 1554 |
| | | 60 | 2136 | 30 | 1059 | 5 | 1615 |
| | | | | 60 | 2751 | 30 | 10330 |
| EFP GF 2 × 1.5M | 682 | 0 | 912 | 0 | 488 | 0 | 1504 |
| | | 60 | 3716 | 30 | 3025 | 5 | 1878 |
| | | | | 60 | 3673 | 30 | 4288 |
| EFP GF 1 × 1.5M | 684 | 0 | 279 | 0 | 444 | 0 | 1498 |
| | | 60 | 580 | 30 | 751 | 5 | 1411 |
| | | | | 60 | 3000 | 30 | 4698 |

With respect to glucose stimulated insulin secretion (GSIS), 0 refers to time 0; 5 refers to 5 minutes post glucose stimulation; 30 refers to 30 minutes post glucose stimulation; 60 refers to 60 minutes post glucose stimulation; PV TC EFP, prevascularized TheraCyte under the epididymal fat pad; PV TC SQ, prevascularized TheraCyte subcutaneous; nPV TC + holes EFP, non-prevascularized TheraCyte perforated under the epididymal fat pad; and EFP GF, epididymal fat pad on Gelfoam, 2 × 1.5M, two constructs with approximately 1.5 × 10$^6$ cells.

The pancreatic progenitor cells were allowed to develop and mature in vivo and insulin secretion and glucose responsiveness of the now mature hormone-secreting cells were determined substantially as described in U.S. application Ser. No. 11/773,944, entitled METHODS OF PRODUCING PANCREATIC HORMONES and Kroon et al. 2008, supra. See Table 1. Additionally, to determine the integrity of the devices, some animals were sacrificed and immunohistochemical examination of the devices was performed.

Applicants previously demonstrated that serum human C-peptide levels below 50 pM, or insulin levels below 25 pM, are insignificant to demonstrate that insulin-secreting cells are responsive to glucose in vivo. This same standard was used in these studies. The results of the studies are shown in Table 1. Both the original Theracyte device and the modified Theracyte device after 8, 12 and 15 weeks had comparable serum human C-peptide levels (animal nos. 675-676 & 679-681), with the exception of animal number 681 at 30 minutes post glucose stimulation whereby the serum C-peptide levels was much higher than any other animal at that time period.

First with regard to the integrity of the TheraCyte encapsulating device, standard hematoxylin and eosin stains of the original Theracyte device and the modified Theracyte device (animal nos. 675-676 and 679-681, respectively) were performed. Microscopic examination of these devices showed that the original Theracyte devices have various host vasculature structures including vascular type cells surrounding the device, but these similar structures were not observed invading the inner cell impermeable membrane and into the space containing the hES-derived cells. That is, there was no host vasculature structures observed inside the inner cell impermeable membrane housing the hES-derived cells, or the graft. In contrast, microscopic examination of the modified Theracyte devices showed that not only was there host vasculature structures associated on the outside of the device, but there were vasculature structures and vascular cells found inside the perforated inner cell impermeable membrane. Hence, the original TheraCyte devices can wholly contain the hES-derived cells and host cells and tissues were not observed in the space housing the hES-derived cells.

In summary, the TheraCyte device is capable of wholly encapsulating (isolating) the hES-derived cells in vivo and the pancreatic progenitors can survive and mature to functioning hormone-secreting cells in vivo in these devices.

In addition to demonstrating the integrity of the TheraCyte device, the present studies also demonstrate that the wholly intact devices allow for sufficient oxygen and various nutrients exchanged between the contained hES-derived cells and the host milieu, and the pancreatic progenitors are capable of surviving and maturing in vivo. For example, serum human C-peptide levels in the prevascularized devices at 9 and 12 weeks were not as robust as the equivalent time point as compared to the controls (animals 682 and 684). However, by the 15$^{th}$ week (post-implant with cells), serum human C-peptide levels in the prevascularized devices were comparable to the unencapsulated (Gelfoam) controls.

Further, animals with the original Theracyte (prevascularized) devices were sacrificed and the devices (or explants) extracted (animal nos. 675 & 676). Immunohistochemistry was performed substantially again as described in and Kroon et al. 2008, supra by fixing the extracted devices and/or the explants and cutting the 10-sections into thin micrometer sections. Sections were washed with PBS twice, followed by PBST (PBS/0.2% (wt/vol) Tween20; Thermo Fisher Scientific). Blocking was done for 1 h at 24° C. with 5% normal donkey serum (Jackson Immuno Research Labs)/PBSTr (PBS/0.1% (wt/vol) Triton X-100 (Sigma)). Primary and secondary antibodies were diluted in 1% BSA (Sigma)/PBSTr for grafts. Primary antibodies were incubated at 4° C. overnight and secondary antibodies for about 1 h 15 min in a moisture chamber. The following primary antibodies and dilutions were used; guinea pig anti-insulin (INS), 1:500 (Dako,A0564); rabbit anti-somatostatin (SST), 1:500 (Dako, A0566); goat anti-somatostatin (SST), 1:300 (Santa Cruz Biotechnology, SC-7819); goat anti-glucagon (GCG), 1:100 (Santa Cruz Biotechnology, SC-7780). Imaging was done by confocal microscopy (Nikon, Eclipse 80i, Ci).

Immunohistochemical examination of the original Theracyte devices/explants clearly demonstrated singly-positive hormonal cells, e.g., GCG, INS and SST expressing cells. This data supports the serum human C-peptide data demonstrating glucose responsiveness of the transplanted hES-derived cells. The presence of hormone-secreting cells demonstrates that pancreatic progenitors are capable of survival and maturation in vivo, even when wholly encapsulated.

The above studies clearly demonstrate the efficacy of both the original and modified TheraCyte devices to wholly contain the hES-derived pancreatic progenitor cells without host cellular invasion across the inner cell impermeable membrane. These studies also demonstrate that the devices inner cell impermeable membrane, although impermeable to cells, is permeable to oxygen and various nutrients required for hES-derived pancreatic progenitor survival in the device such that the progenitor cells are capable of maturing to hormone-secreting cells in vivo, which are cells are function and are responsive to glucose.

Further, it is envisioned that the pancreatic-lineage cell populations, in particular, at least the pancreatic progenitors described herein, will also mature and function in vivo when encapsulated in the improved devices, for example at least those described in FIGS. 1-11.

EXAMPLE 2

Encapsulated Pancreatic Progenitors Function In Vivo in the in the Absence of Host-Graft Cell Contact To determine whether host-graft cell-to-cell contact was required for in vivo functioning of transplanted pancreatic progenitor cell populations, cells were loaded into non-prevascularized cell encapsulation devices.

Pancreatic progenitor cell populations were generated substantially as described above in Example 1. No devices in this study were prevascularized, and all TheraCyte devices (4.5 μL) were loaded ex vivo with at least $1.5 \times 10^6$ cells (1.5M) or $4.5 \times 10^6$ cells (4.5M) in each device. Three devices containing 1.5M cells were implanted subcutaneously (TC SQ 1.5M), and 3 devices containing $4.5 \times 10^6$ cells (4.5M), or about 15 μL, were implanted subcutaneously (TC SQ 4.5M) ex vivo. In contrast and as controls, animals with implanted unencapsulated pancreatic progenitors were carried along side the encapsulated, but not prevascularized, experiments. Three mice were each implanted subcutaneously with two Gelfoam constructs loaded with about $1.9\text{-}2.4 \times 10^6$ cells (total for two constructs), or about 4 μL/construct, and 2 mice were implanted under the EFP with two Gelfoam constructs loaded with about with about $1.9\text{-}2.4 \times 10^6$ cells (total for two constructs), or about 4 μL/construct. Table 2 summarizes the results of the above experiments.

TABLE 2

Human C-peptide serum levels from encapsulated non-prevascularized mature pancreatic hormone-secreting cells

| Implant | Animal # | GSIS time (min) | 6 wk Cpep (pM) | 8.5 wk Cpep (pM) | 10 wk Cpep (pM) |
|---|---|---|---|---|---|
| SQ 1.5M | 833 | 0 | nd | 3.5 | 20.9 |
| | | 60 | 5.8 | 60.9 | 167.7 |
| | 834 | 0 | nd | 0.3 | 32.5 |
| | | 60 | 0.6 | 32.6 | 97.5 |
| | 835 | 0 | 102.8 | 168.3 | 153.1 |
| | | 60 | 77.2 | 197.8 | 440.0 |
| SQ 4.5M | 836 | 0 | nd | 11.4 | 39.3 |
| | | 60 | nd | nd | 29.9 |
| | 837 | 0 | 6.8 | 60.9 | 85.8 |
| | | 60 | 8.3 | 137.3 | 188.4 |
| | 838 | 0 | 4.2 | 21.6 | 64.4 |
| | | 60 | 39.5 | 36.4 | 98.0 |
| SQ GF 1.9-2.4M | 819 | 0 | nd | 26.9 | 0.4 |
| | | 60 | 4.2 | 26.9 | 79.4 |
| | 820 | 0 | nd | 4.7 | 11.8 |
| | | 60 | 4.2 | 20.7 | 12.9 |
| | 821 | 0 | nd | 10.9 | 12.3 |
| | | 60 | 2.7 | 69.1 | 54.3 |
| EFP GF 1.9-2.4M | 822 | 0 | nd | 22.5 | 57.3 |
| | | 60 | 4.7 | 95.0 | 132.8 |
| | 823 | 0 | nd | 11.8 | 33.5 |
| | | 60 | 46.0 | 243.3 | 170.3 |

With respect to glucose stimulated insulin secretion (GSIS), 0 refers to time 0; 60 refers to 60 minutes post glucose stimulation; SQ, subcutaneous device; SQ GF, subcutaneous Gelfoam, EFP GF, EFP, epididymal fat pad Gelfoam; 1.5M, $1.5 \times 10^6$ cells; 4.5, $4.5 \times 10^6$ cells; 1.9-2.4M, $1.9\text{-}2.4 \times 10^6$ cells; nd, none detected.

Although Example 1 demonstrated that hES-derived cells can survive, mature and function in vivo in prevascularized devices, based on Table 2 prevascularization is not essential for cell survival, growth and/or maturation. Table 2 compares encapsulated pancreatic progenitor cells with unencapsulated pancreatic progenitor cells on Gelfoam, the later has been well documented to produce functioning hormone secreting cells in vivo, see Kroon et al. 2008 supra. In fact, at 60 minutes post glucose-stimulation, serum C-peptide levels from the encapsulated cells were comparable to serum C-peptides levels observed from cells which were unencapsulated. Compare animal numbers 833-838 to animal numbers 819-823. In fact, the encapsulated cells performed better than the unencapsulated when implanted subcutaneously, e.g. compare animal numbers 833-835 (TC SQ 1.5M) to 819-821 (SQ 1.9-2.4M). Thus, host-graft cell-to-cell contact is not essential because as clearly demonstrated in this example, transplanted wholly encapsulated cells survive, grow and mature in the absence of any host-graft cell-to-cell contact all together.

The methods, compositions, and devices described herein are presently representative of preferred embodiments and are exemplary and are not intended as limitations on the scope of the patent. Changes, alternatives, modifications and variations therein and other uses will occur to those skilled in the art which are encompassed within the spirit of the invention and are defined by the scope of the disclosure. For example, TheraCyte devices come in 4.5 μL, 20 μL, and 40 μL sizes, and therefore one of ordinary skill in art can scale-up the above studies if employing a device which is capable of containing more cells. Further, since Kroon et al. 2008 supra has demonstrated the efficacy of pancreatic progenitors in rescuing streptozotocin (STZ) induced diabetic mice before and after graft implantation, one of ordinary skill in the art can perform analogous studies using the encapsulated cells described herein. Also, methods of purifying or enriching for certain hES-derived populations are described in detail in U.S. application Ser. No. 12/107,020, entitled METHODS FOR PURIFYING ENDODERM AND PANCREATIC ENDODERM CELLS DERIVED FROM HES CELLS, filed Apr. 8, 2008, which is herein incorporated by reference in its entirety. Thus, one of ordinary skill in the art can enrich for specific hES-derived cells including but not limited to, pancreatic progenitor cells, pancreatic endocrine precursor cells and/or endocrine precursor cells.

EXAMPLE 3

Cryopreserved Pancreatic Progenitors when Implanted Develop and Function In Vivo Because cell transplantation is hindered by the lack of available cell sources and operational and logistical problems, there is a need to provide an unlimited cell source for transplantation at times convenient to the patient.

Human ES cells were differentiated substantially as described in Examples 1 and 2 and Kroon et al., 2008, supra, as well as in Tables 3a-h below. At day 14 of differentiation, the pancreatic progenitors were centrifuged and then resuspended in freezing media containing DMEM with 30% Xeno-free Knockout Serum Replacement, 25 mM HEPES and 10% dimethyl sulfoxide solution. Cells were aliquoted into freezing vials. Cells were equilibrated in freezing medium for about 15 minutes at ambient temperature, then 45 minutes at 4° C., then placed on ice and put in a programmed freezer which was equilibrated to 0° C.

The cells and the freezing chamber were brought to −9° C. at a rate of 2° C./min. The chamber and the sample were held at this temperature for about 10 minutes, and the vials were seeded manually. The sample was held at −9° C. for about 10 minutes and then cooled at a rate of 0.2° C./minute until the sample reached −40° C. The freezing chamber was subsequently cooled at a rate of 25° C./minute until the sample reached about −150° C. The vialed cells were then moved to the vapor phase of a liquid nitrogen storage freezer.

At desired times, the vials was rapidly thawed by transferring the cells to a 37° C. water bath. The cells were transferred to a 15 ml sterile tube, containing DMEM with B-27 (1:100) and KGF+EGF (each at 50 ng/mL), mixed gently and spun briefly at 50×g. Supernatant was removed and cells were resuspended in the same buffer plus DNAse at 25 µg/mL and placed in rotation culture.

Cell survival was quantitated by photographing the pancreatic progenitor aggregates when they have been swirled to the center of the tissue culture well, promptly upon thawing before any significant cell loss has occurred, and at 4 days post-thaw when the decrease in cell mass has completed. The area occupied by the cells in the photographs was quantitated, and expressed as a percent survival at 4 days post-thaw. In this example, at least 52% survival was obtained. The morphology of cultured pancreatic progenitor cells after cryopreservation and thawing was identical to that of fresh cells.

After 4 days of post-thaw culturing, the cells were loaded in devices substantially as described above and surgically implanted in the mammal as described above. The cryopreserved cells were capable of developing and maturing into functioning hormone secreting and acinar cells of the pancreas in vivo similar to that described for fresh pancreatic progenitor cell aggregates. See Example 4.

Hence, cryopreservation of in vitro human pancreatic progenitors derived from hES cells has little or no effect on development after implantation. Thus, cryopreservation proves to be a reliable method of storing hESC-derived pancreatic progenitor cells suitable for transplantation.

EXAMPLE 4

Methods of Providing for Human Pancreatic Progenitors for the Treatment of Diabetes Pluripotent Stem Cell Culture Conditions Culturing, proliferation and maintenance of pluripotent stem cells, in particular ES and IPS cells, are performed substantially as described in D'Amour et al. 2005 & 2006 and Kroon et al. 2008, supra. ES base medium of DMEM-F12/1% Glutamax/1% Non-essential amino acids/1% Pen-Strep/ 0.2% b-mercaptoethanol was used. For stage 0 or proliferation of hES cells, various growth factors and or insulin and insulin-like growth factors levels were kept very low. Feeder-free pluripotent stem cells were cultured using low levels of human serum. The pluripotent stem cells were maintained using a Rho-kinase inhibitor Y27632. It will be appreciated that other Rho-kinase inhibitors can be used with similar results. The ES or pluripotent stem cell culture conditions are substantially similar to Examples 1 and 2 as described above.

It will be appreciated that the ES base medium can routinely contain about 20% Knockout Serum Replacement (KSR) or Xeno-free (XF) Knockout serum replacement.

It will be appreciated that hES cell cultures routinely contain about 0 ng/mL, about 4 ng/ml or about 10 ng/mL basic fibroblast growth factor (bFGF). As previously demonstrated, under certain conditions low levels of Activin A help promote pluripotent stem cell proliferation without promoting hES cell differentiation. Hence, pluripotent stem cell cultures typically contain about 5 ng/mL, about 10 ng/mL or about 20 ng/mL of Activin A or B, or other similarly biologically active TGF-β growth factor families, for example, at least GDF-8 and GDF-11. Still in other pluripotent stem cell cultures, an Errb2-binding ligand such as heregulin at low levels also helps to promote hES cell proliferation, for example, at about 5 to 10 ng/mL. Also, any combination of different or low levels of bFGF, Activin A, B or other TGF-β growth factor family members, specifically GDF-8 and -11, and Errb2-binding ligands such as heregulin can be employed to promote hES cell cultures, so long as low levels of the growth factors are maintained as to promote proliferation of hES cells and their pluripotency and not differentiation of the cells thereof. Embodiments described herein describe various growth factors (in some cases large proteins) in maintaining and proliferating pluripotent stem cell cultures, however, the high cost of these proteins on a large-scale manufacturing basis makes is cost-prohibitive. As such, identifying and characterizing certain small molecules to replace the larger growth factor proteins may be beneficial. One such molecule is nor-epinephrine (NE), which is described in more detail in U.S. Application 61/172,998, titled SMALL MOLECULES SUPPORTING PLURIPOTENT CELL GROWTH AND METHODS THEREOF, and filed 27 Apr. 2009, and is herein incorporated by reference in its entirety. In one embodiment, about 5 ng/mL, about 10 ng/mL, about 20 ng/mL, about 30 ng/mL, about 40 ng/mL, about 50 ng/mL, about 60 ng/mL, about 70 ng/mL, about 80 ng/mL, about 90 ng/mL, about 100 ng/mL or more is employed to maintain pluripotent stem cultures, for example, hES or iPS cultures. In one preferred embodiment, about 50 ng/mL can be employed in hES cell cultures.

It will be appreciated that proliferation of pluripotent stem cells are routinely sustained on fibroblast feeder cells, Alternatively, ES cells can be cultured on an extracellular matrix coated plates (Corning). Further, Bodnar et al. (Geron Corporation, Menlo Park, Calif., USA) describe growing hES cell cultures on a monolayer of extracellular matrix, which matrix was derived by lysing fibroblast feeder layer in U.S. Pat. No. 6,800,480, the disclosure of which is herein expressly incorporated by reference. However, in a preferred embodiment, feeder-free pluripotent stem cells are cultured using low levels of human serum, for example, about 0.1%, about 0.2%, about 0.3%, about 0.4%, about 0.5%, about 0.6%, about 0.7%, about 0.8%, about 0.9%, about 1%, about 1.2%, about 1.4%, about 1.6%, about 1.8%, about 2% to about 10% or more in a base ES cell medium. Human serum can be added to the base media simultaneously thereby obviating any need to pre-coat tissue culture dishes as contemplated in U.S. Pat. No. 6,800,480 or that provided by Corning. Use of human serum for culturing, maintaining and proliferation of pluripotent stem cell cultures is described in more detail in U.S. application Ser. No. 11/875,057, entitled METHODS AND COMPOSITIONS FOR FEEDER-FREE PLURIPOTENT STEM CELL MEDIA CONTAINING HUMAN SERUM, filed on 19 Oct. 2007, which is herein incorporated by reference in its entirety.

Pluripotent stem cells can also be maintained with the addition of a Rho kinase family of inhibitors, for example at least Y27632. Y27632 has recently been found to prevent apoptosis, as well as enhance the survival and cloning efficiency of dissociated human pluripotent stem cells without affecting self-renewal properties or pluripotency. Although, embodiments described herein use Y27632 due to its commercial availability, other Rho kinase inhibitors can be employed and still be within the scope of the invention.

Pluripotent Stem Cell Differentiation Conditions for Stage 1

Directed differentiation of pluripotent stem cells, in particular ES and IPS cells, were performed substantially as described in D'Amour et al. 2005 & 2006 and Kroon et al. 2008, supra and in above related U.S. Applications, including U.S. Application 61/171,759, titled CELL COMPOSITIONS DERIVED FROM DEDIFFERENTIATED REPROGRAMMED CELLS, filed 22 Apr. 2009, which are herein incorporated by reference in their entireties.

Prior to differentiation Stage 1, or at day 0 of the differentiation process, pluripotent stem cells were cultured in a medium comprising of RPMI1640/1% Glutamax/1% Pen-Strep and substantially no serum and/or about 0.1% Bovine Serum Albumin (BSA). Also, 1:5000 or 1:1000 or about 0.02% or 0.1%, respectively, of Insulin/Transferrin/Selenium (ITS) supplement was added. In addition, various growth factors including a TGF-β super family growth factor and a Wnt family member were added to the differentiation medium.

It will be appreciated that the added TGF-β super family growth factors include but are not limited to Activin A, Activin B, GDF-8 or GDF-11. In some embodiments a Wnt pathway activator can be used. In another embodiment, Wnt-3a is used in conjunction with one of the TGF-β super family growth factors. In a further preferred embodiment, about 50 ng/mL of Wnt3a is employed with about 100 ng/mL of a TGF-β super family member such as Activin A, Activin B and GDF-8 and -11. Still in another embodiment, small molecules which activate similar signal transduction pathways can be substituted for the growth factors. See, for example, Borowiak, M. et al. (2009) describing two small molecules which direct differentiation of mouse and human embryonic stem cells to endoderm. Borowiak, M. et al. (2009) Cell Stem Cell, 4(4):348-358 is herein incorporated by reference in its entirety.

The pluripotent cells were incubated in the above media conditions for at least 24 hours, after which time the medium was exchanged to a medium comprising RPMI1640/1% Glutamax/1% Pen-Strep and a slight increase in FBS, approximately 0.2% FBS and further containing about 100 ng/mL of a TGF-β super family member. A Wnt family member was not added. It will be appreciated that a Wnt family member may be added to the culture after about 24 hours.

The cells were cultured in this medium for another 24 hours. After about a total of 48 hours since the cells had been differentiation (day 0 to day 2), the cells in the culture comprise differentiated definitive endoderm cells.

It will be appreciated that the total number of days of differentiation in stage 1, starting with day 0 (pluripotent stem cells), can be about 1-3 days, preferably about 1-2 days, and even more preferable, about 2 days. It will be appreciated that after stage 1 differentiation, the cells in the culture will comprise about 10%, about 20%, about 30%, about 40%, about 50%, about 60%, about 70%, about 80%, about 90%, about 95%, about 96%, about 97%, about 98% or about 99% differentiated definitive endoderm cells Methods for determining the composition of the cultures has been previously described in the above related applications, but principally by RNA and protein assays well known in the art. Definitive endoderm cells express increased levels of certain signature cell surface markers such as SOX17 and FOXA2, but can also express increased levels of CER and CXCR4, but do not appreciably express HNF4-α which is expressed appreciably in foregut endoderm (or PDX1-negative foregut) cells. Definitive endoderm cells also do not appreciably express markers observed in later Stage 3, 4 or 5 cells such as or PDX1, NNF6, SOX9 and PROX 1 expressed in PDX1-positive foregut endoderm cells, or PDX1, NKX6., PTF1A, CPA and cMYC expressed in PDX1-positive pancreatic progenitor or PDX1/NKX6.1 co-positive pancreatic progenitor cells, or NGN3, PAX4, ARX and NKX2.2 expressed in endocrine precursor cells, or INS, GCG, GHRL, SST or PP expressed in polyhormonal or singly hormonal pancreatic endocrine cells.

Differentiation Conditions for Stage 2

After about 48 hours (about 2 days) of differentiation of pluripotent stem cells to DE, the DE differentiation media was replaced by another media condition which promotes human foregut endoderm (PDX1-negative foregut endoderm) formation or Stage 2 cells. This cell culture medium comprises RPMI1640/1% Glutamax/1% Pen-Strep and 0.2% FBS or a further increase in FBS, e.g. about 2% FBS. Similar to the above Stage 1 culture medium, about 1:5000 or 1:1000 or about 0.02% or 0.1%, respectively, of ITS supplement was added.

It will be appreciated that the DE differentiation media is not always supplemented with ITS.

However, DE differentiation growth factors such as TGF-β super family growth factors or Wnt family members were intentionally not included in the medium. A TGF-β kinase inhibitor was added to the medium.

Because removal of TGF-β super family members is beneficial for proper foregut endoderm formation, use of TGF-β super family member inhibitors such as a TGF-β kinase inhibitors, ensures that the effects of the action of TGF-β super family members are substantially inhibited. This allows efficient direct differentiation of the DE to foregut endoderm (PDX1-negative foregut endoderm) without the lingering effects of DE differentiation in the culture.

Instead of TGF-β super family members, keratinocyte growth factor (KGF) was added to the culture to promote foregut endoderm formation. Cells were incubated in this media for about 24 hours, after which the media was replaced with substantially the same media except that now the TGF-β kinase inhibitor was removed from the culture. The cells were then incubated in this media (minus TGF-β kinase inhibitor) for 5 days with media changes.

It will be appreciated that the cells can be incubated in this media (minus TGF-β kinase inhibitor) for up to about 3 days for Stage 2 with permissible media changes. The total number of days of differentiation, starting with day 0 and pluripotent stem cells, is about 3-5 days, preferably about 4-5 days, and more preferable, about 5 days.

Again, methods for determining the composition of the cultures has been previously described in the above related applications, but principally by RNA and protein assays well known in the art. Foregut endoderm cells, or PDX1-negative foregut endoderm cells, express increased levels of certain signature cell surface markers such as Sox17, HNF3-β and HNF4-α. This is distinguished from DE of Stage 1 which does not appreciably express HNF4-α, but does appreciably express the other two markers, Sox17 and HNF3-β. PDX1-negative foregut cells also do not appreciably express markers observed in later Stage 3, 4 or 5 cells such as or PDX1, NNF6, SOX9 and PROX 1 expressed in PDX1-positive foregut endoderm cells, or PDX1, NKX6.1, PTF1A, CPA and cMYC expressed in PDX1-positive pancreatic progenitor or PDX1/NKX6.1 co-positive pancreatic progenitor cells, or NGN3, PAX4, ARX and NKX2.2 expressed in endocrine precursor cells, or INS, GCG, GHRL, SST or PP expressed in polyhormonal or singly hormonal pancreatic endocrine cells.

Differentiation Conditions for Stage 3

To promote differentiation of PDX1-positive foregut endoderm cells from PDX1-negative foregut endoderm cells of Stage 2, the PDX1-negative foregut endoderm cell culture medium was exchanged and incubated in a medium comprising DMEM high glucose/1% Glutamax/1% Pen-Step/1% B27 Supplement with either about 1 or 2 uM of Retinoic Acid (RA), about 0.25 uM of KAAD-Cylcopamine and with or without about 50 ng/mL of Noggin. Alternatively, some cultures instead of receiving RA, received 1 nM to about 3 nM of aromatic retinoid (E)-4-[2-(5,6,7,8-tetrahydro-5,5,8,8-tetramethyl-2-naphthylenyl)-1-propenyl] benzoic acid (TTNPB). Still other cultures received about 1 mM of dorsomorphin. The cells were incubated in this culture medium for about 3 days. It will be appreciated that cells can be incubated about 1-5 days, preferably 2-4 days, and more preferably 3 days.

Similar to the above, methods for determining the composition of the cultures has been previously described in the above related applications, but principally by RNA and protein assays well known in the art. PDX1-positive foregut endoderm cells express increased levels of certain signature cell surface markers besides PDX1 such as Sox9, HNF6 and PROX1, but do not appreciably express other markers of later Stage 4 or 5 cells such as or PDX1, NKX6.1, PTF1A, PCA and cMYC found in pancreatic progenitor cells, or NGN3, PAX4, ARX and NKX2.2 expressed in endocrine precursor cells, or INS, GCG, GHRL, SST or PP expressed in polyhormonal or singly hormonal pancreatic endocrine cells.

Differentiation Conditions for Stage 4

To further promote differentiation of properly differentiated PDX1/NKX6.1 co-positive pancreatic progenitor cells from PDX1-positive foregut endoderm cells, the PDX1-positive foregut endoderm cell culture medium was exchanged and incubated in a medium comprising a similar base medium as in Stage 3 above, DMEM high glucose/1% Glutamax/1% Pen-Step/1% B27 Supplement, except that there is no RA or retinoic acid derivative such as TTNPB or noggin or dorsomorphin. Instead, about 50 ng/mL of Noggin, KGF and FGF was added to the culture. It will be appreciated that about 10 to 100 ng/mL of epidermal and fibroblast growth factors (EGF and FGF) can be added to the culture. There is preferably about 10 to 50 ng/mL, or preferably, about 10 ng/mL of EGF and about 50 ng/mL of FGF added to the cultures. Alternatively no FGF can be added to the cultures, or about 25 to 100 ng/mL each of Noggin, KGF, FGF, or preferably about 50 ng/mL of Noggin, KGF and FGF was used. The cells were kept in this medium with media exchanges for about 4 to 5 days. It will be appreciated that cells can be kept in medium for about 2 to 6 days, preferably 3 to 5 days, and even more preferably 4 to 5 days with permissible media exchange.

Similar to the above, methods for determining the composition of the cultures has been previously described in the above related applications, but principally by RNA and protein assays well known in the art. PDX1/NKX6.1 co-positive pancreatic progenitor or endoderm cells express increased levels of certain signature cell surface markers such as PDX1, NKX6.1, PTF1A, CPA and cMYC, but do not appreciably express other markers found in later stage cells such as NGN3, PAX4, ARX and NKX2.2 expressed in endocrine precursor cells, or INS, GCG, GHRL, SST or PP expressed in polyhormonal or singly hormonal pancreatic endocrine cells.

Transplantation & Purification of PDX1-Positive Pancreatic Progenitors

After about 3-5 days in the Stage 4 cell culture medium, the cell cultures were either prepared for: i) flow cytometry separation and/or purification and analysis; ii) encapsulation into cell encapsulation devices as discussed in more detail above; and/or iii) transplanted into the mammal. Alternatively, the cell culture from Stage 4 was transferred or adapted in media of DMEM high glucose/1% Glutamax/1% Pen-Step/1% B27 Supplement minus the growth factors for about 1 to 2 days, before flow cytometry and/or transplantation.

Detailed descriptions for enriching, separating, isolating and/or purifying pancreatic progenitors and/or pancreatic endocrine cells or endocrine precursor cells are described in detail in U.S. application Ser. No. 12/107,020, entitled METHODS FOR PURIFYING ENDODERM AND PANCREATIC ENDODERM CELLS DERIVED FROM hES CELLS, filed 8 Apr. 2008, which is herein incorporated by reference in its entirety.

Briefly, CD142 was used to enrich for PDX1-positive pancreatic progenitor (or pancreatic epithelia cells or PE) by quickly washed with PBS and enzymatically dissociated into a substantially single cell suspension using TrypLE and 3% FBS/PBS/1 mM EDTA (sorting buffer). The single cell suspension was passed through a 40-100 uM filter and then pelleted and washed again in a sorting buffer, re-pelleted and then resuspended again as a substantially single cell suspension in sorting buffer at about $1\times10^8$ cells/mL. The resuspended cells were then incubated with Phycoerythrin conjugated anti-mouse CD142 antibody (BD Pharmigen™) at 10 ul per $1\times10^7$ cells. The cells were washed at least once with volume sorting buffer, pelleted and resuspended again as a substantially single cell suspension in sorting buffer containing a solution of anti-Phycoerythrin microbeads (Miltenyi Biotec) and incubated. Cells were washed at least once and immuno-magnetic selection of CD142-positive cells was performed. The pre-sort, bound and flow through fractions were each collected and counter-stained with anti-PDX1 and/or anti-CHGA.

The bound fraction was highly enriched for CD142-positive cells and for PDX1-positive pancreatic progenitor cells as compared to the pre-sorted and flow through fractions. See Table 9 of U.S. application Ser. No. 12/107,020. For example, the anti-CD 142-positive or bound fraction was comprised of about 71% PDX1-positive pancreatic progenitor cells as compared to about 22% PDX1-positive pancreatic progenitor cells in the pre-sort fraction and about 8% PDX1-positive pancreatic progenitor cells in the flow through fraction. Hence, there was about a 3-fold enrichment in PDX1-positive pancreatic progenitor cells in the anti-CD142-positive or bound fraction relative to the pre-sort population. Also, the CD142-positive or bound fraction was depleted of chromograninA (CHGA)-positive cells indicating that multi- or singly-hormonal endocrine cells were not selected or enriched in this population. CD142 therefore can be used for positive immuno-selection to enrich and/or purify for PDX1-positive pancreatic progenitors or epithelial cells, whereas the flow through fraction (the fraction or cells not binding to the antibody column; or CD142-) is enriched with pancreatic endocrine type cells. Also, refer to Table 10 of U.S. application Ser. No. 12/107,020.

EXAMPLE 5

In Vivo Maturation of Pancreatic Progenitors Ameliorates Hypoglycemia in Diabetic Induced Animals To determine whether the PDX1-positive pancreatic progenitor cell cultures or enriched populations, including the cryopreserved populations, were fully capable of developing and maturing in vivo to glucose sensitive insulin secreting cells, the progenitor populations were loaded into the encapsulating devices similar to that described above in Examples 1 and 2 using either a Hamilton syringe with a blunted appropriately sized gauge needle or centrifuge loading method per the manufacturer's procedure.

Before loading the cells into the device, the device was deemed suitable for transplantation and use in mammals including humans, e.g., the device has passed typical standards of quality control including sterilization. Because membrane components of the device are likely to be comprised of hydrophobic membranes, e.g. PTFE and therefore repel water, sterilizing the devices is typically accomplished by wetting the devices in an alcohol solvent (e.g. 95% ETOH) and then washing them in saline solution repeatedly. Devices therefore should be kept moist prior to loading. Ideally any device loading method is performed under sterile conditions ensuring that any device component which is implanted will not be contaminated with unwanted cells.

Device loading can be performed by either using a Hamilton syringe or the like plus a blunted appropriately sized gauge sterile needle (size will vary depending on the diameter of the port of the device) or the like, e.g., a 22 gauge needle. The needle is connected to a the appropriate Hamilton syringe and contains about 5, 10, 15, 20, 25, 30, 35, 40, 45, 50, 55, 60, 65, 70, 75, 80, 85, 90, 95, 100 or more μL of cell volume which reflects a therapeutically effective amount or dose of cells. The needle is then inserted through at least one a port of the device and through to the lumen (or chamber or reservoir) but without touching the walls of device. Substantially the entire contents of the syringe are expelled slowly into the device while at the same time the needle is being withdrawn.

Alternatively, another method of loading the device using a needle is by using a sterile plastic or silicone port tube which connects the device port to the needle which is inserted into the port but not in the lumen. In this method, a silicone adhesive is injected into the silicone port tube, walling or sealing off the device port. The port tube is then cut off and inspected for leaks or breaches.

To load the device using a centrifuge method, a certain cell volume containing a therapeutically effective amount or dose of cells is drawn up in a micropipette tip and the tip contacted with the device port. The device and the pipette tip can also be put into a larger container or centrifuge conical tube, either immobilized or not. Often certain volumes of media is layered on top of the cell suspension in the pipette tip and also in the larger conical tube. The conical tube in then centrifuge at about 1000 rpms for a few minutes, preferably 20 seconds up to about 2 minutes or until cells are loaded into the device. Then great care is used to remove the loading components and secure the loaded device.

The encapsulated cells in the device were then prepared for implantation into a mammal, e.g., immuno-compromised mice such as SCID/Bg, rat, larger mammal or human patient. Methods of implanting the encapsulated cells and device is substantially as that described above in Examples 1 and 2 and Kroon et al., 2008, except in Kroon et al. the cells are implanted on a GELFOAM and not contained inside a device. However, because the encapsulated cell population contains substantially a progenitor population similar to that described by Kroon et al. 2008 and U.S. Pat. No. 7,534,608, titled METHODS OF PRODUCING PANCREATIC HORMONES, filed Jul. 5, 2007, which is herein incorporated by reference in its entirety, assays for determining cell functionality were substantially the same. Briefly, the animals were tested about every two, three or four weeks by injecting them with a bolus of arginine or glucose, preferably glucose, which if the encapsulated cells have properly matured into now beta cells in vivo, will secrete insulin in response to the glucose. In short, the mature beta cells are responsive to glucose not unlike naturally occurring beta cells. Blood was collected from the mammal to determine levels of human C-peptide which is secreted from the human transplanted progenitor cells having matured into human beta cells. Human C-peptide was detected in animal serum as early as 4 to 6 weeks after transplantation and the levels of human C-peptide increase over time as more progenitors or endocrine precursor cells mature into properly functioning beta cells. Typically amounts of human C-peptide above 50 pM were considered an indication of function of the transplanted cells. It was previously shown that engrafted cells from the PDX1-positive pancreatic progenitors faithfully give rise to endocrine cells expressing markers and physiological characteristic of functioning pancreatic hormone-secreting cells. See Kroon et al. 2009, supra and U.S. application Ser. No. 11/773,944, titled METHODS OF PRODUCING PANCREATIC HORMONES filed Jul. 5, 2007, which is herein incorporated by reference in its entirety.

Immuno-suppression is contemplated for certain mammals for an initial interim period until the progenitors inside the device fully mature and are responsive to glucose. In some mammals immuno-suppression regimens may be for about 1, 2, 3, 4, 5, 6 or more weeks, and likely depend on the mammal.

Lastly, similar to Kroon et al. 2008, the encapsulated cells not only matured into pancreatic islet clusters with endocrine cells but also developed into islet associated cells such as acinar cells. Thus, the transplanted PDX1-positive pancreatic progenitors were not committed to becoming just singly-hormonal endocrine secreting cells but were capable of maturing and developing into what is substantially similar to a human islet, comprising both endocrine and acinar cells. And this in vivo maturation and glucose responsiveness of the transplanted cells was observed whether the progenitor cells (PDX1/NKX6.1 co-positive; endocrine precursors, or certain poly-hormonal or singly-hormonal cells) were cultured and differentiated in vitro and subsequently transplanted, or whether certain progenitors were purified or enriched before transplantation, or whether they were previously made from one or more batches and cryopreserved, thawed and adapted in culture before transplantation.

Briefly, after transplant, the transplanted cells were allowed to differentiate and further mature in vivo. To determine whether the transplanted cells had normal physiological function as a naturally occurring beta cell for example, levels of human insulin were determined by testing levels of human C-peptide. Human C-peptide is cleaved or processed from human pro-insulin, hence, the detection of human C-peptide, and not endogenous mouse C-peptide, indicates that insulin secretion is derived from the grafted (exogenous) cells.

Glucose stimulated human C-peptide secretion of the transplanted cells in serum was measured at various time points post transplant. It will be appreciated that glucose stimulated human C-peptide secretion can be measured at various time points, e.g. at least 30, 35, 40, 45, 50, 55, 60, 65 and more days. Glucose stimulated human C-peptide levels could be acutely measured in the serum as early as about 15 minutes post-glucose administration or injection. Blood was withdrawn from the animals at about 15, 30 and 60 minutes time intervals post glucose administration. The serum was separated from the blood cells through centrifugation in micro-containers as described by the manufacturer (Becton Dickinson). The ELISA analysis was performed of the serum using ultrasensitive human specific C-peptide ELISA plates (Alpco). In general, more than the majority of animals receiving the encapsulated transplanted cells responded to glucose as demonstrated by levels greater than threshold levels 50 pM of human C-peptide.

In summary, wholly encapsulated cells by the above device does not affect maturation of the cells nor the physiological function of the cells once they have matured. Further, the amelioration of hypoglycemia in these diabetic induced animals was observed and was substantially similar to that previously described in Kroon et al. (2008) supra, as well as in U.S. Pat. No. 7,534,608, although neither described wholly encapsulated transplanted cells or grafts. These references are herein incorporated by reference in their entireties.

Accordingly, it will be apparent to one skilled in the art that varying substitutions, modifications or optimization, or combinations may be made to the embodiments disclosed herein without departing from the scope and spirit of the invention.

All publications and patents mentioned in this specification are herein incorporated in their entireties by reference.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

What is claimed is:

1. A method for producing insulin in vivo in a mammal, said method comprising:
   (a) providing an in vitro human pancreatic and duodenal homeobox gene 1 (PDX1)-positive pancreatic progenitor cell population into an implantable semi-permeable device, wherein the semi-permeable device comprises a first seal at a peripheral edge of the semi-permeable device, thereby forming at least one chamber for encapsulating living cells, and at least a second seal which effectively reduces the volume of the encapsulating chamber;
   (b) implanting the device containing the progenitor cell population into a mammalian host; and
   (c) maturing the progenitor cell population in said device in vivo such that there is no cell-to-cell contact between the progenitor cell within the device and the host cell in the mammal and the resulting cell population comprises endocrine and acinar cells, wherein at least some of the endocrine cells are insulin secreting cells that produce insulin in response to glucose stimulation in vivo, thereby producing insulin in vivo to the mammal.

2. The method of claim 1, further comprising maturing PDX1-positive pancreatic progenitor cells to acinar or duct cells.

3. The method of claim 1, wherein the device is first pre-vascularized by implanting in the mammal before introducing progenitor cells.

4. The method of claim 1, wherein the device comprises a plurality of welds for maximizing surface area to volume ratio of the human PDX1-positive pancreatic progenitor cell population in the device.

5. The method of claim 1, wherein the device comprises a plurality of welds to increase vascularization by the host.

6. The method of claim 1, wherein the device is refillable.

7. The method of claim 1, wherein the device is expandable.

8. The method of claim 1, wherein the in vivo cell population is monitored.

9. The method of claim 1, wherein greater than 25 pM of insulin is detectable in the serum of the mammal post glucose-stimulation.

10. The method of claim 1, wherein greater than 50 pM of human C-peptide is detectable in the serum of the mammal post glucose-stimulation.

11. The method of claim 1, wherein the mammal is immuno-suppressed.

12. The method of claim 1, wherein providing a human PDX1-positive pancreatic progenitor cell population comprises thawing a cell population.

13. The method of claim 1, wherein providing a human PDX 1-positive pancreatic progenitor cell population further comprises enriching the cell population for PDX1/NKX6.1 co-positive pancreatic progenitor cells.

14. The method of claim 1, wherein providing a human PDX1-positive pancreatic progenitor cell population further comprises enriching the cell population for PDX1/NKX6.1 co-positive pancreatic progenitor cell by contacting the cell population with an antibody that binds to CD142 antigen and enriching for said CD142 binding cells.

15. The semi-permeable device of claim 1, wherein the semi-permeable device comprises a semi-permeable membrane.

16. The semi-permeable membrane of claim 15, wherein the semi-permeable membrane comprises a vascularizing means and nutrient and oxygen exchange means.

* * * * *